United States Patent
Paydar et al.

(10) Patent No.: US 9,587,878 B2
(45) Date of Patent: Mar. 7, 2017

(54) MEDICATION DISPENSING CART

(75) Inventors: Akbar Paydar, Mountain View, CA (US); Stanley Kim, Mountain View, CA (US); Chris Richardson, Mountain View, CA (US); Gerardo Moreno, Mountain View, CA (US); Victor Santini, Mountain View, CA (US); Nathaniel Moody, Mountain View, CA (US); Laszlo Virag, Mountain View, CA (US); Len Hom, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 33 days.

(21) Appl. No.: 13/312,817

(22) Filed: Dec. 6, 2011

(65) Prior Publication Data

US 2012/0203377 A1    Aug. 9, 2012

Related U.S. Application Data

(60) Provisional application No. 61/420,262, filed on Dec. 6, 2010.

(51) Int. Cl.
*G06F 17/00* (2006.01)
*F25D 29/00* (2006.01)
(Continued)

(52) U.S. Cl.
CPC ........... *F25D 29/008* (2013.01); *F25D 29/00* (2013.01); *G01K 3/005* (2013.01); *G01K 3/04* (2013.01);
(Continued)

(58) Field of Classification Search
CPC .... G07F 9/105; G07F 11/002; G07F 17/0092; F25D 29/008; Y10T 307/352; G01K 3/005; G01K 3/04
(Continued)

(56) References Cited

U.S. PATENT DOCUMENTS 4,202,586 A    5/1980    Oplinger
4,368,867 A    1/1983    Pendleton et al.
(Continued)

FOREIGN PATENT DOCUMENTS

CH    688607 A5    12/1997
DE    8114991 U    10/1981
(Continued)

OTHER PUBLICATIONS

International Search Report and Written Opinion of PCT/US11/63597, mailed Apr. 13, 2012, 15 pages.
(Continued)

*Primary Examiner* — Michael K Collins
(74) *Attorney, Agent, or Firm* — Kilpatrick Townsend & Stockton LLP

(57) ABSTRACT

Embodiments of the invention provide medication dispensing carts and methods. The medication dispensing carts may include a base having wheels that allow the carts to be transported within a facility, a computing device configured to receive input from a user, a display device communicatively coupled with the computing device for displaying information to the user, a post that couples the display device with the base, and a plurality of cassettes that have one or more bins within which medical supplies are stored. The plurality of cassettes may be coupled with the post and the post may include a plurality of communication ports that communicatively couple one or more of the cassettes with the computing device to perform or provide various functions.

30 Claims, 22 Drawing Sheets

(51) Int. Cl.

| | | |
|---|---|---|
| *G01K 3/00* | (2006.01) | |
| *G01K 3/04* | (2006.01) | |
| *G07F 9/10* | (2006.01) | |
| *G07F 11/00* | (2006.01) | |
| *G07F 17/00* | (2006.01) | |
| *G06F 19/00* | (2011.01) | |

(52) U.S. Cl.
CPC .......... *G06F 19/3462* (2013.01); *G07F 9/105* (2013.01); *G07F 11/002* (2013.01); *G07F 17/0092* (2013.01); *A61B 50/10* (2016.02); *A61B 50/30* (2016.02); *A61B 2050/0014* (2016.02); *Y10T 307/352* (2015.04)

(58) Field of Classification Search
USPC .......................................... 700/242, 243, 232
See application file for complete search history.

(56) References Cited

U.S. PATENT DOCUMENTS

| | | |
|---|---|---|
| 4,372,515 A | 2/1983 | Noonan |
| 4,471,931 A | 9/1984 | Covey et al. |
| D279,007 S | 5/1985 | Empson et al. |
| 4,556,189 A | 12/1985 | Kirpluk et al. |
| 4,561,620 A | 12/1985 | Goetz et al. |
| 4,575,033 A | 3/1986 | Henneberg et al. |
| 4,589,621 A | 5/1986 | Hunt et al. |
| 4,616,218 A | 10/1986 | Bailey et al. |
| 4,640,199 A | 2/1987 | Zigman |
| 4,645,153 A | 2/1987 | Granzow et al. |
| D289,873 S | 5/1987 | Gemmell et al. |
| 4,681,378 A | 7/1987 | Hellman, III |
| D293,382 S | 12/1987 | Ichikawa |
| 4,717,112 A | 1/1988 | Pirkle |
| 4,726,633 A | 2/1988 | Noble et al. |
| 4,729,533 A | 3/1988 | Hillary et al. |
| D295,415 S | 4/1988 | Thies et al. |
| 4,769,634 A | 9/1988 | Killian, Jr. et al. |
| 4,834,329 A | 5/1989 | Delapp |
| 4,836,478 A | 6/1989 | Sweere |
| 4,836,486 A | 6/1989 | Vossoughi et al. |
| 4,852,500 A | 8/1989 | Ryburg et al. |
| 4,918,841 A | 4/1990 | Turner et al. |
| 4,919,387 A | 4/1990 | Sampson |
| D310,358 S | 9/1990 | Nuttall et al. |
| 4,967,928 A | 11/1990 | Carter |
| D312,630 S | 12/1990 | Esslinger |
| 4,989,291 A | 2/1991 | Parent |
| D317,912 S | 7/1991 | Takai |
| D319,405 S | 8/1991 | Brawne |
| D319,435 S | 8/1991 | Brown |
| 5,039,928 A | 8/1991 | Nishi et al. |
| 5,041,770 A | 8/1991 | Seiler et al. |
| D326,847 S | 6/1992 | Savio |
| 5,174,223 A | 12/1992 | Nagy et al. |
| 5,217,064 A | 6/1993 | Kellow et al. |
| D337,104 S | 7/1993 | Orchard |
| D339,796 S | 9/1993 | Goodner et al. |
| 5,260,885 A | 11/1993 | Ma |
| 5,277,392 A | 1/1994 | Rossman et al. |
| 5,282,678 A * | 2/1994 | Teufel et al. .................. 312/221 |
| 5,287,815 A | 2/1994 | Gross |
| D344,933 S | 3/1994 | Wiseman et al. |
| 5,321,579 A | 6/1994 | Brown et al. |
| D348,449 S | 7/1994 | Rodd et al. |
| D349,489 S | 8/1994 | Wang |
| 5,362,025 A | 11/1994 | Trom et al. |
| D354,052 S | 1/1995 | Imai |
| D354,952 S | 1/1995 | Rodd |
| D357,468 S | 4/1995 | Rodd |
| 5,437,235 A | 8/1995 | Randolph |
| 5,442,512 A | 8/1995 | Bradbury |
| 5,466,058 A | 11/1995 | Chan |
| 5,473,997 A | 12/1995 | Solomon et al. |
| 5,522,323 A | 6/1996 | Richard |
| 5,536,084 A | 7/1996 | Curtis et al. |
| D377,720 S | 2/1997 | Miller et al. |
| 5,630,566 A | 5/1997 | Case |
| 5,687,717 A | 11/1997 | Halpern et al. |
| 5,694,199 A | 12/1997 | Rodriguez |
| D393,382 S | 4/1998 | Rutter et al. |
| 5,738,316 A | 4/1998 | Sweere et al. |
| 5,772,637 A | 6/1998 | Heinzmann et al. |
| 5,775,234 A | 7/1998 | Solomon et al. |
| 5,806,943 A | 9/1998 | Dell et al. |
| 5,822,185 A | 10/1998 | Cavello |
| 5,842,672 A | 12/1998 | Sweere et al. |
| 5,868,079 A | 2/1999 | Charny |
| 5,897,179 A | 4/1999 | Wade |
| 5,918,841 A | 7/1999 | Sweere et al. |
| 5,960,901 A | 10/1999 | Hanagan |
| 5,971,341 A | 10/1999 | Pfister |
| 5,992,953 A | 11/1999 | Rabinovitz |
| 6,022,088 A | 2/2000 | Metzler |
| 6,029,580 A | 2/2000 | Alfonso et al. |
| 6,061,104 A | 5/2000 | Evanicky et al. |
| 6,085,972 A | 7/2000 | Wright |
| 6,098,936 A | 8/2000 | Birrell |
| 6,117,126 A * | 9/2000 | Appelbaum ............ A61B 17/00 600/301 |
| 6,170,929 B1 | 1/2001 | Wilson et al. |
| 6,175,779 B1 | 1/2001 | Barrett |
| 6,199,952 B1 | 3/2001 | Davis |
| 6,269,753 B1 | 8/2001 | Roddan |
| 6,298,794 B1 | 10/2001 | Brown et al. |
| 6,339,732 B1 | 1/2002 | Phoon et al. |
| 6,389,992 B1 | 5/2002 | Miller |
| 6,394,402 B2 | 5/2002 | Coonan et al. |
| 6,431,580 B1 | 8/2002 | Kady |
| 6,435,109 B1 * | 8/2002 | Dell et al. ................. 108/144.11 |
| 6,493,220 B1 * | 12/2002 | Clark et al. ............. 361/679.41 |
| 6,557,955 B2 | 5/2003 | Saravis |
| 6,604,019 B2 | 8/2003 | Ahlin et al. |
| 6,626,445 B2 | 9/2003 | Murphy et al. |
| 6,721,178 B1 * | 4/2004 | Clark et al. ................ 361/679.4 |
| 6,775,591 B1 | 8/2004 | Shoenfeld |
| 6,816,145 B1 | 11/2004 | Evanicky |
| 6,996,455 B2 * | 2/2006 | Eggenberger et al. ........ 700/231 |
| 7,009,840 B2 | 3/2006 | Clark et al. |
| 7,134,673 B2 | 11/2006 | Ferraro et al. |
| 7,142,944 B2 * | 11/2006 | Holmes et al. ............... 700/237 |
| 7,154,397 B2 | 12/2006 | Zerhusen et al. |
| 7,594,668 B2 * | 9/2009 | Arceta et al. .............. 280/47.35 |
| 7,630,791 B2 | 12/2009 | Nguyen et al. |
| 7,747,347 B2 * | 6/2010 | Park, IV ........................ 700/243 |
| 7,952,315 B2 * | 5/2011 | Park, IV ........................ 318/578 |
| 8,140,187 B2 * | 3/2012 | Campbell et al. ............ 700/242 |
| 8,180,485 B2 * | 5/2012 | Reckelhoff .......... A61G 12/001 700/237 |
| 8,196,939 B2 | 6/2012 | Bustle et al. |
| 8,210,548 B1 * | 7/2012 | Agyemang ............. B62B 3/005 280/47.35 |
| 8,378,620 B2 * | 2/2013 | Reckelhoff .................... 320/101 |
| 8,412,375 B2 | 4/2013 | Schifman et al. |
| 8,773,270 B2 * | 7/2014 | Paydar ................... G01K 3/005 340/5.73 |
| 8,812,153 B2 * | 8/2014 | Reckelhoff .......... A61G 12/001 700/237 |
| 2001/0002448 A1 * | 5/2001 | Wilson et al. ................. 700/233 |
| 2001/0032035 A1 * | 10/2001 | Holmes et al. ................ 700/231 |
| 2002/0000092 A1 | 1/2002 | Sharood et al. |
| 2002/0074905 A1 | 6/2002 | Tiramani et al. |
| 2002/0171332 A1 | 11/2002 | Skov et al. |
| 2003/0159076 A1 | 8/2003 | Delisle et al. |
| 2005/0062238 A1 * | 3/2005 | Broadfield ............ A61G 12/001 280/1 |
| 2005/0140510 A1 | 6/2005 | Elwood et al. |
| 2005/0279122 A1 | 12/2005 | Cohen et al. |
| 2006/0005876 A1 | 1/2006 | Gaudiana et al. |
| 2006/0125356 A1 * | 6/2006 | Meek et al. ................... 312/215 |
| 2006/0179571 A1 * | 8/2006 | Newkirk ............................ 5/600 |
| 2007/0069491 A1 | 3/2007 | Ferraro et al. |
| 2007/0228680 A1 * | 10/2007 | Reppert et al. ............. 280/47.35 |

(56) References Cited

U.S. PATENT DOCUMENTS

| | | | |
|---|---|---|---|
| 2009/0037020 A1* | 2/2009 | Brown | G07F 17/0092 700/240 |
| 2009/0132090 A1 | 5/2009 | Kaczmarz et al. | |
| 2009/0159608 A1 | 6/2009 | Shoenfeld | |
| 2009/0231132 A1 | 9/2009 | Shoenfeld | |
| 2009/0262266 A1* | 10/2009 | Harbin | H02J 7/0045 349/1 |
| 2009/0312656 A1 | 12/2009 | Lau et al. | |
| 2009/0319094 A1* | 12/2009 | Park, IV | 701/1 |
| 2010/0004780 A1* | 1/2010 | Rickelhoff | A61G 12/001 700/231 |
| 2010/0042437 A1 | 2/2010 | Levy et al. | |
| 2010/0102280 A1* | 4/2010 | Ford et al. | 252/502 |
| 2010/0106291 A1 | 4/2010 | Campbell et al. | |
| 2010/0218021 A1 | 8/2010 | Ma et al. | |
| 2010/0222649 A1 | 9/2010 | Schoenberg | |
| 2010/0241446 A1 | 9/2010 | Eckert et al. | |
| 2010/0275625 A1 | 11/2010 | Lowenstein | |
| 2010/0300130 A1 | 12/2010 | Shoenfeld et al. | |
| 2012/0176245 A1 | 7/2012 | Paydar et al. | |
| 2012/0203377 A1* | 8/2012 | Paydar | G01K 3/005 700/232 |
| 2012/0245731 A1 | 9/2012 | Reckelhoff | |
| 2013/0345861 A1* | 12/2013 | Rickelhoff | A61G 12/001 700/242 |
| 2014/0172158 A1* | 6/2014 | Paradissis | G01K 3/005 700/232 |
| 2015/0100154 A1* | 4/2015 | Rickelhoff | A61G 12/001 700/243 |

FOREIGN PATENT DOCUMENTS

| | | |
|---|---|---|
| DE | 295 06 433 U1 | 8/1995 |
| DE | 195 36 664 A1 | 4/1997 |
| DE | 196 42 425 A1 | 4/1998 |
| DE | 196 50 100 A1 | 6/1998 |
| EP | 0 145 410 A2 | 6/1985 |
| EP | 0 321 137 A2 | 6/1989 |
| EP | 0 796 575 A1 | 9/1997 |
| EP | 1690617 A2 | 8/2006 |
| FI | 974408 A | 6/1999 |
| JP | 5161510 A | 6/1993 |
| JP | 9262137 A | 10/1997 |
| JP | 10-011172 | 1/1998 |
| JP | 10-057157 A | 3/1998 |
| JP | 10-146224 A | 6/1998 |
| JP | 11-127976 A | 5/1999 |
| JP | 2007-326653 A | 12/2007 |
| WO | 97/46824 A1 | 12/1997 |
| WO | 2007/095222 A2 | 8/2007 |
| WO | 2012/078611 A1 | 6/2012 |
| WO | 2012/078676 A1 | 6/2012 |

OTHER PUBLICATIONS

International Search Report and Written Opinion of PCT/US11/63505, mailed Apr. 26, 2012, 9 pages.

Advertisement for Ergotron Mobile Work Centers, Integrated Design and Manufacturing, Feb. 1997, 1 page.

Author Unknown, "24" Wide AnthroCart", Anthro Technology Furniture, Date Unknown, [retrieved on Mar. 19, 2007], 4 pages. Retrieved from: http://web.archive.org/web/19970521181347/www.anthro.com/hprods_a/p_3.html.

Author Unknown, "All the Right Moves . . . ," Flat Panel Monitor Mounting Solutions, Ergotron, Inc., 1997, 4 pages.

Author Unknown, "CMS Business," Fieldlink, Ergotron Nov. 1997, 3 pages.

Author Unknown, "Computer/Storage Cart," Milcare, Inc., 1997, 2 pages.

Author Unknown, "Ergotron ErgoCart," Product Bulletin, Ergotron, Inc., Dec. 1997, 2 pages.

Author Unknown, "Ergotron ErgoLift," Product Bulletin, Ergotron, Inc., Apr. 1999, 3 pages.

Author Unknown, "Evaluation Program: Mobile WorkCenter Solutions," Ergotron, Inc., 1997, 5 pages.

Author Unknown, "Flat Panel Monitor, Keyboard & Laptop," ARMS Product Guide, Ergotron, Inc., 1997, 8 pages.

Author Unknown, "Ira Goldklang's TRS-80 Revived Site: Model 200 Page," Aug. 5, 2007, [retrieved on Mar. 24, 2008], 3 pages. Retrieved from: http://www.trs-80.com/trs80-models-model200.htm.

Author Unknown, "Korean Makers of TFT-LCD Likely to Have Brisk Year," AsiaPulse News, Jan. 11, 1999, 1 page.

Author Unknown, "MediComp 2001 Options and Accessories," JACO, Inc., 1997, 1 page.

Author Unknown, "MLT 2001: Variable Height Laptop/Peripheral Cart," Jaco Inc., 1997, 3 pages.

Author Unknown, "Mobile WorkCenter System,"Ergotron, Inc., 1997, 5 pages.

Author Unknown, "Mobile WorkCenters: Featuring Ergotron's Patented Monitor Suspension System," Ergotron, Inc., 1994, 4 pages.

Author Unknown, "PCT-SC: Ergonomically designed Trans-Mobile self-contained clinical computing workstation system," Tremont Medical, 1997, 2 pages.

Author Unknown, "Point-of-Care Carts as part of a Clinical Information System," MMP MedCart, date unknown, 8 pages.

Author Unknown, "Point-of-Care: Cart Systems," MMP MedCart, 1997, 2 pages. Retrieved from: http://web.archive.org/web/19970301233615/www.medcart.com/pointof.html.

Author Unknown, "Technology Furniture," Anthro, Date Unknown, 40 pages.

Author Unknown, "Technology Furniture: New Product Update Fall 1996," Anthro, 1996, 12 pages.

Author Unknown, "The Ergotron ErgoCart: A mobile and height adjustable solution for an entire computer system," Product Sheet, Ergotron, Inc., May 1999, 2 pages.

Author Unknown, "The Ergotron ErgoCart: A Mobile Solution for an entire computer system," Product Sheet, Ergotron, Inc., Apr. 1998, 2 pages.

Author Unknown, "The Nursing Station on Wheels," Infoport, Sculptor Development Technologies, Inc., Date Unknown, [retrieved on Mar. 24, 2008], 2 pages. Retrieved from: http://www.sculptorsoftware.com/infoport.asp.

Author Unknown, "Welcome to Ergotron," Ergotron, Inc., 1996, [retrieved on Sep. 17, 2008], 1 page. Retrieved from: http://web.archive.org/web/19961104052222/http://www.ergotron.com/.

Bassak, G., "Sharp picture, Fuzzy Forecasting," Business & Company Resource Center, Electronic Buyers' News, Jan. 31, 2000, 3 pages.

International Search Report and Written Opinion of PCT/US07/76336 mailed on Aug. 13, 2008, 6 pages.

International Search Report and Written Opinion of PCT/US07/03765 mailed on Jun. 3, 2008, 4 pages.

U.S. Appl. No. 13/312,374, filed Dec. 6, 2011, Non-Final Office Action mailed Oct. 7, 2013, 27 pages.

U.S. Appl. No. 13/312,374, filed Dec. 6, 2011, Notice of Allowance mailed Feb. 28, 2014, 14 pages.

U.S. Appl. No. 13/461,615, filed May 1, 2012, Non-Final Office Action mailed Dec. 5, 2012, 24 pages.

U.S. Appl. No. 13/461,615, filed May 1, 2012, Advisory Action mailed May 21, 2013, 4 pages.

U.S. Appl. No. 13/461,615, filed May 1, 2012, Notice of Allowance mailed Mar. 7, 2014.

Office Action issued on Dec. 1, 2015 in JP Patent Application No. 2013-543289, filed Dec. 6, 2011.

Notification to Make Divisional Application issued May 6, 2015 for CN patent application No. 103339663 A, 3 pages.

First Office Action issued Aug. 4, 2015 for CN application No. 103339663 A, 11 pages.

Patent Examination Report No. 1 issued Jun. 30, 2015 for AU patent application No. 2011338557, 3 pages.

* cited by examiner

MEDICATION DISPENSING CART

CROSS-REFERENCES TO RELATED APPLICATIONS

This application claims priority to Provisional U.S. Patent Application No. 61/420,262 filed Dec. 6, 2010, entitled "Medication Dispensing Cart." This application is also related to U.S. patent application Ser. No. 12/278,263 filed on Feb. 12, 2007, by Rickelhoff, entitled "Medication Dispensing Cart;" and further related to Provisional U.S. Patent Application No. 60/839,104 filed Aug. 21, 2006, by Rickelhoff, entitled "Solar Charged Mobile Working Stations."

The entire disclosures of all of the aforementioned Provisional and Non-Provisional U.S. Patent Applications are hereby incorporated by reference, for all purposes, as if fully set forth herein.

BACKGROUND OF THE INVENTION

The invention relates generally to mobile carts and more specifically to mobile medication carts for dispensing medication to patients in hospitals, nursing homes, rehabilitation centers, and/or other care facilities.

In the health care industry, an important component of patient care is providing and administering the proper medications and/or medical treatments, such as delivering drugs, applying or replacing bandages, treating wounds, and the like. Medications or treatments, in the form of pills (e.g., capsules, liquids, and the like), injections, inhalants, topical medications, bandages, and the like are given to patients to relieve pain, to prevent or eliminate infections, to care for wounds, to promote healing, and/or to treat illnesses and disease. Administering medications may involve delivering determined doses at specified intervals throughout the day and/or night over one or several days, weeks, or months depending on the condition being treated.

Some medications should not be taken together due to potential adverse reactions, or are carefully controlled because of their potential effect on the body or their potential for misuse or abuse. In addition, if the wrong medication is administered to a patient, or if the correct medication is given but in too large a dosage or too frequently, adverse effects may result. Accordingly, it is important that doctors, nurses, staff, management, and the like of hospitals and other care facilities (e.g., nursing homes) ensure that patients take only prescribed medications in accordance with their prescriptions. Usually, administrative controls and paper records, sometimes augmented by security measures, are used to achieve these objectives. However, due to the importance of properly administering the correct medications to the correct patient in the correct doses, there remains a need for improved methods of delivering medications to patients in a controlled manner.

BRIEF SUMMARY OF THE INVENTION

Embodiments of the invention provide medication dispensing carts and methods. According to one aspect, embodiments of the invention provide a medication dispensing cart that may include a base having wheels that allow the medication dispensing cart to be moved within a facility. The medication dispensing cart may also include a computing device configured to receive input from a user and a monitor communicatively coupled with the computing device for displaying information to the user. The medication dispensing cart may further include a post that couples the monitor with the base. The post may include a plurality of communication ports that couple with cassettes. The medication dispensing cart may additionally include a plurality of cassettes each having at least one bin within which medical supplies are stored. The plurality of cassettes may be coupled with the post and at least one of the plurality of cassettes may be communicatively coupled with the computing device via one of the communication ports of the post.

In some embodiments, one or more of the cassettes include a guide light that is configured to illuminate to display a location of a bin of the cassette. The medication dispensing cart may additionally include a stand-by button that sets the monitor in a stand-by mode when activated so that information is not displayed on the monitor when in the stand-by mode. The medication dispensing cart may additionally include a stand-by indicator configured to display a first display when the monitor is in the stand-by-mode and a second display when the monitor is not in the stand-by mode.

The medication dispensing cart may additionally include a power system controller and at least one battery. The power system controller may be configured to adjust the power usage of the medication dispensing cart or adjust a power discharge setting of the battery based on an operational need of the medication dispensing cart or a condition of the battery. In some embodiments, the medication dispensing cart may include two batteries that provide power to the medication dispensing cart. One of the batteries may be removable from the medication dispensing cart without adversely affecting the power provided to the medication dispensing cart. The medication dispensing cart may also include a housing within which the battery or batteries are inserted. The housing may include a latch mechanism to lock the battery within the housing. One or both of the batteries may be a hot swappable smart battery and the power system controller may include an interface port that communicatively couples the power system controller with the smart battery. The smart battery may include a gauge (e.g., a gas gauge or other energy gauge) to generate readings of the battery's remaining capacity. In some embodiments, the medication dispensing cart may additionally include a backup battery configured to allow access to one or more of the bins during a power failure of the medication dispensing cart.

In some embodiments, the cassettes are coupled with the post to form a cassette stack. The cassette stack may include a combination of large cassettes and small cassettes or only include large or small cassettes. The large cassettes may include bins ranging in height between about 4 inches and about 8 inches, and preferably about 6 inches, and the small cassettes may include bins ranging in height between about 2 inches and about 4 inches, and preferably about 3 inches. In some embodiments, the post includes a backplane that includes the plurality of communication ports that couple with the cassettes. The computing device or backplane may be configured to determine a cassette configuration of the plurality of cassettes when the plurality of cassettes are coupled with the post. In some embodiments, the monitor includes a discharge element coupled to a touch screen. The discharge element may be configured to dissipate a static charge generated by a user of the medication dispensing cart or the touch screen. In some embodiments, the medication dispensing cart may be one of a plurality of medication dispensing carts wirelessly networked with a central administrator system that centrally controls one or more aspects or functions of the medications dispensing cart and/or centrally gathers, monitors, and/or stores information related to the medication dispensing cart and/or a patient associated therewith. In some embodiments, medication dispensing cart can persist data through network outages, transferring information from the cart to the central administration system, or any server, and/or from the central administration system, or server, to the cart when a network connection (wireless or wired) is restored.

According to another aspect, embodiments of the invention may provide a method of configuring a medication dispensing cart. The method may include providing a medication dispensing cart that includes a cassette system controller, a base, a monitor that displays information to a user, and a post that couples the monitor with the base. The post may have at least one interface port that communicatively couples the cassette system controller with one or more cassettes. The method may also include providing a plurality of cassettes that each include at least one bin within which medical supplies are stored and coupling each of the plurality of cassettes with the post so that the plurality of cassettes form a cassette stack and so that at least one of the cassettes is communicatively coupled with the cassette system controller via the at least one interface port.

The method may further include identifying with the cassette system controller a type of the at least one cassette communicatively coupled with the cassette system controller and/or identifying with the cassette system controller a configuration of the cassette stack. The method may additionally include configuring the cassette system controller to operate with the at least one cassette based off the identification of the type of the at least one cassette. In some embodiments, identifying the type of the at least one cassette may include: determining a size of the cassette from among a plurality of different sized cassettes, determining that the cassette comprises a patient-specific bin, and/or determining that the cassette comprises a utility specific bin. In some embodiments, identifying a configuration of the cassette stack may include determining an arrangement of different sized cassettes in the cassette stack and/or determining an association between a patient and a cassette designated to store medical supplies specifically for the patient.

According to another aspect, embodiments of the invention may provide a method of configuring a medication dispensing cart that may include providing a medication dispensing cart comprising a cassette system controller, providing a plurality of cassettes that each include at least one bin within which medical supplies are stored, coupling each of the plurality of cassettes with the medication dispensing cart so that the plurality of cassettes form a cassette stack and so that at least one of the cassettes is communicatively coupled with the cassette system controller, and identifying with the cassette system controller either or both: a type of the at least one cassette communicatively coupled with the cassette system controller and/or a configuration of the cassette stack.

The method may also include decoupling a first battery from the medication dispensing cart without adversely affecting an amount of power provided to the medication dispensing cart. The first battery may be one of a plurality of batteries providing the amount of power to the medication dispensing cart and the medication dispensing cart may be operated based entirely or essentially entirely off battery power. The method may further include queuing information related to the medication dispensing cart or a patient on a storage medium of the medication dispensing cart when a central administrator system is offline and transmitting the information to the central administrator system when the central administrator system is online.

According to another aspect, embodiments of the invention may provide a method of providing power to a medication dispensing cart. The method may include providing a medication dispensing cart comprising a power system controller, providing a plurality of cassettes that each include at least one bin within which medical supplies are stored, coupling each of the plurality of cassettes with the medication dispensing cart, and coupling at least one battery with the power system controller. The power system controller may be configured to adjust a power usage of the medication dispensing cart or adjust a power discharge of the at least one battery based on an operational need of the medication dispensing cart or a condition of the battery.

In some embodiments, the medication dispensing cart may include at least two batteries coupled with the power system controller and the method may also include decoupling a first battery from the power system controller while the medication dispensing cart is operational without adversely affecting an amount of power provided to the medication dispensing cart. The medication dispensing cart may be operated based entirely or substantially off battery power. In some embodiments, the medication dispensing cart may further include a cassette system controller and the plurality of cassettes may be coupled with the medication dispensing cart so that at least one of the cassettes is communicatively coupled with the cassette system controller. In such embodiments, the method may further include identifying (with the cassette system controller) either or both: a type of the at least one cassette communicatively coupled with the cassette system controller and/or a configuration of the cassette stack.

According to another aspect, embodiments of the invention may provide a medication dispensing cart including a base having wheels that allow the medication dispensing cart to be moved within a facility, a computing device configured to receive input from a user, a display device communicatively coupled with the computing device for displaying information to the user, a plurality of cassettes each having at least one bin within which medical supplies are stored, a power system controller, and at least one battery coupled with the power system controller. The power system controller may be configured to adjust a power usage of the medication dispensing cart or adjust a power discharge of the at least one battery based on an operational need of the medication dispensing cart or a condition of the battery.

In some embodiments, the medication dispensing cart may include two batteries that provide power to the medication dispensing cart. One of the batteries, and preferably both batteries, may be removable from the medication dispensing cart during operation of the medication dispensing cart without adversely affecting the power provided to the medication dispensing cart. The medication dispensing cart may also include a housing within which the battery (or batteries) is inserted. The housing may include a latch mechanism to lock the battery within the housing. The battery, and preferably both batteries, may be a hot swappable smart battery and the power system controller may include an interface port that communicatively couples the power system controller with the smart battery.

In some embodiments, the medication dispensing cart may further include a backup battery that is configured to allow access to one or more of the bins during a power failure of the medication dispensing cart, or failure of the batteries powering the medication dispensing cart. In some embodiments, the medication dispensing cart may further include a post that couples the display device with the base. The post may include a plurality of communication ports that couple with cassettes and the plurality of cassettes may be coupled with the post. In such embodiments, at least one of the plurality of cassettes, and preferably all cassettes, may be communicatively coupled with the computing device via one of the communication ports of the post.

According to another aspect, embodiments of the invention may provide a method of providing power to a medication dispensing cart. The method may include providing a medication dispensing cart that includes a power system controller, providing a plurality of cassettes that each include at least one bin within which medical supplies are stored, coupling each of the plurality of cassettes with the medication dispensing cart, and coupling at least one battery with the power system controller. The power system controller may be configured to adjust a power usage of the medication dispensing cart or adjust a power discharge of the at least one battery based on an operational need of the medication dispensing cart or a condition of the battery.

In some embodiments, the medication dispensing cart may include at least two batteries coupled with the power system controller and the method may also include decoupling a first battery from the power system controller while the medication dispensing cart is operational without adversely affecting an amount of power provided to the medication dispensing cart. The first battery may be removed from the medication dispensing cart while the cart is being operated based entirely or substantially off battery power. In some embodiments, the medication dispensing cart may also include a cassette system controller and the plurality of cassettes may be coupled with the medication dispensing cart so that at least one of the cassettes is communicatively coupled with the cassette system controller. In such embodiments, the method may further include identifying, with the cassette system controller, a type of the at least one cassette communicatively coupled with the cassette system controller and/or a configuration of the cassette stack.

BRIEF DESCRIPTION OF THE DRAWINGS

The present invention is described in conjunction with the appended figures.

Figure 1A:
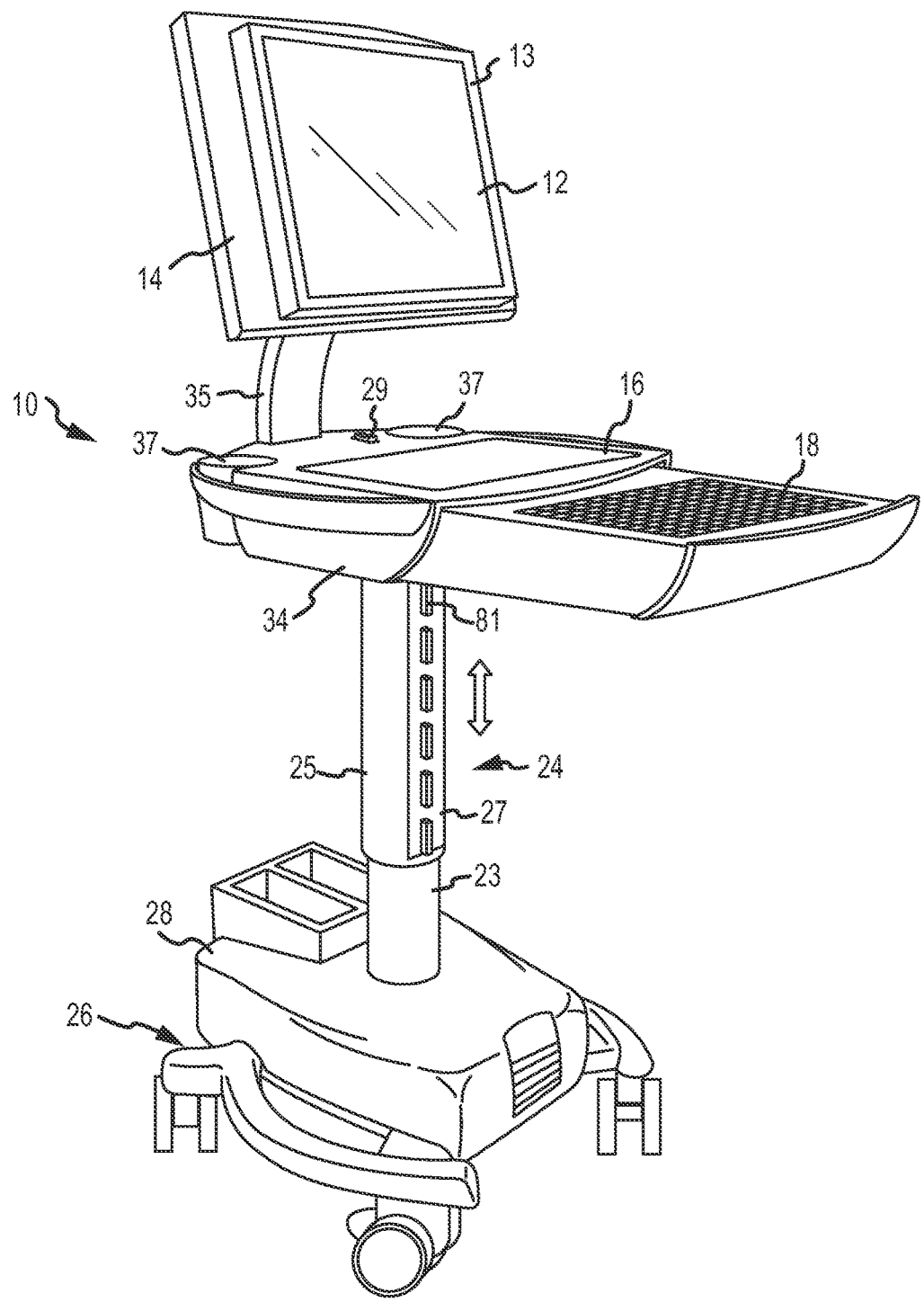
FIGS. 1A-C illustrate various front perspective views of a medication dispensing cart according to an embodiment of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "storage medium" or "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, the process described herein may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In one aspect, embodiments of the invention provide an apparatus for dispensing medication, such as a medication dispensing cart having a computer with a computer monitor and a controller. The medication dispensing cart may include a power system having one or more hot swappable batteries and a power system controller. The medication dispensing cart may also include a cassette system with a cassette controller and one or more individual cassettes. The computer controller, the power system controller, and the cassette controller may be interfaced with the medication dispensing cart. The computer controller may receive computer controller input and generate computer controller output. The power system controller may receive power system input and generate power system output. Further, the cassette controller may receive cassette input and generate cassette output. Although the application generally refers to "cassettes" that are removable from the medication dispensing cart, it should be realized that the cassettes could be or include drawers that are built into the medication dispensing cart. For example, in some embodiments the cassettes are drawers coupled with the cart so that the drawers are not removable from the medication dispensing cart. For convenience the drawers will be referred to herein as "cassettes" although it should be realized that use of non-removable drawers is also contemplated.

In one embodiment, one or more of the cassettes may include a guide light that illuminates when the cassette or a bin of the cassette is accessed so as to visually display the location of the cassette and/or bin. The medication dispensing cart may further include a stand-by button that places the computer monitor in a stand-by mode when pressed, and may include a stand-by indicator associated with the stand-by button. The stand-by indicator may include a first display (e.g., a green LED) that indicates when the stand-by mode is off and a second display (e.g., a red LED) that indicates when the stand-by mode is on.

The hot-swappable battery or batteries may be Li-polymer batteries. In one embodiment, the power system and/or hot-swappable batteries are configured so that a battery may be removed from the power system without affecting the power provided to the medication dispensing cart. The power system may include a battery latch mechanism to lock the hot swappable battery within the power system. The hot swappable battery or batteries may be a smart battery and the power system may include a System Management Bus (SMB) port that allows the power system to communicate with the smart battery(s). The smart battery(s) may also include a gauge (e.g., gas gauge) to generate readings of the battery's remaining capacity.

The power system controller may be communicatively coupled with a backup battery (e.g., a third battery) that is configured to provide access to one or more bins during a power failure of the medication dispensing cart (e.g., the backup battery may provide power to locking mechanisms so that medication stored within the cart can be accessed if the hot-swappable battery(s) fail). The backup battery may also detect and alarm when intrusion or otherwise unauthorized access occurs after the batteries and accessible power sources are removed. The cassettes system may comprise a combination of large cassettes, small cassettes, and the like. In one embodiment, the large cassettes comprise cassettes ranging in height between about 4 inches and about 8 inches and the small cassettes comprise cassettes ranging in height between about 2 inches and about 4 inches.

The medication dispensing cart may additionally include a post having a backplane that communicatively couples with one or more of the cassettes. The backplane may identify the configuration of the cassette system (i.e., the arrangement and number of large and small cassettes included in the cassette system) and/or may identify the size of each of the cassettes of the cassette system (i.e., identify whether each cassette is large or small) when the cassettes are communicatively coupled with the backplane.

The computer monitor may include a discharge element coupled to a touch screen. The discharge element may be configured to dissipate a charge generated by a user of the medication dispensing cart and/or the touch screen.

Figure 1B:
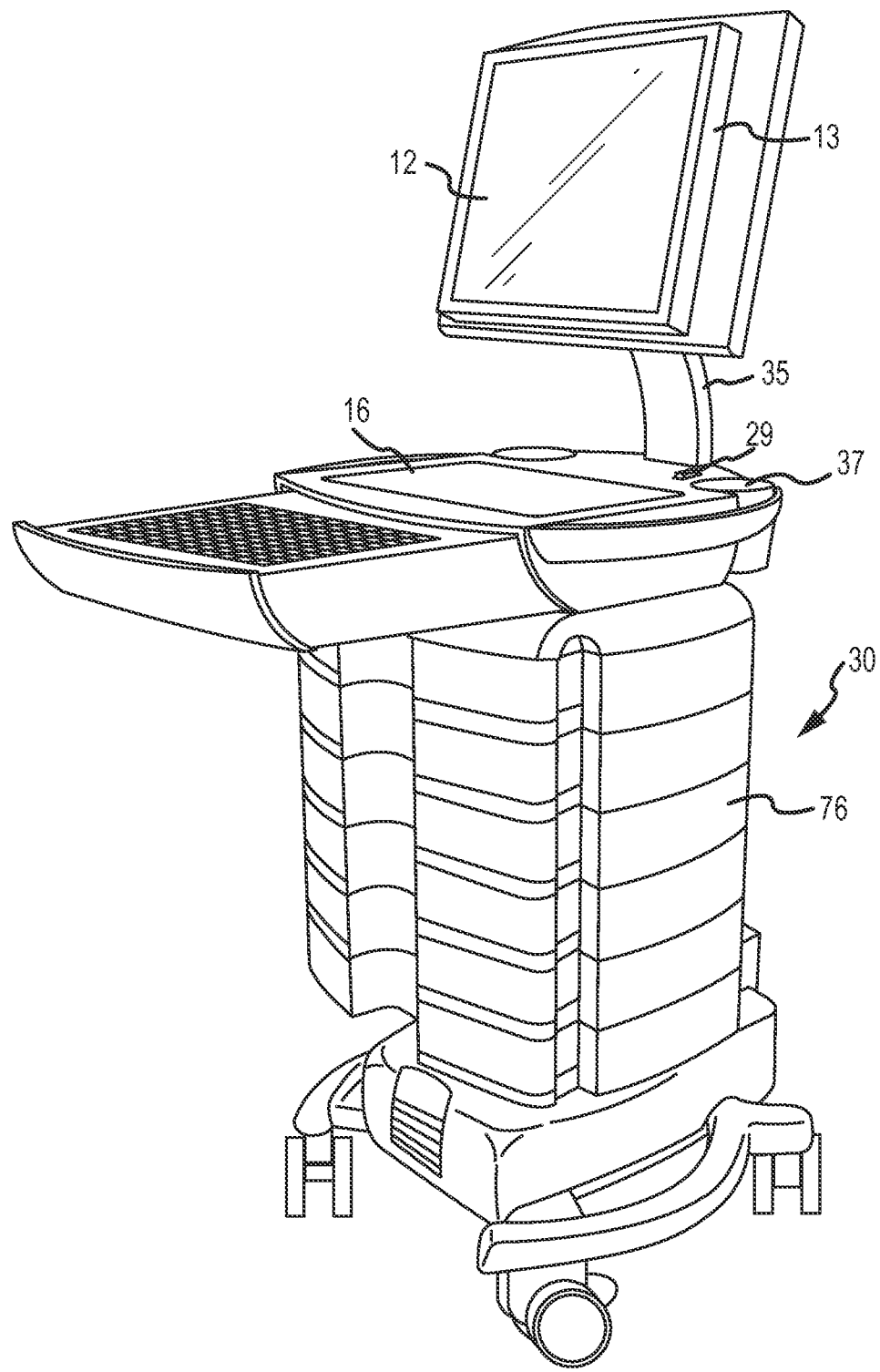
Figure 1C:
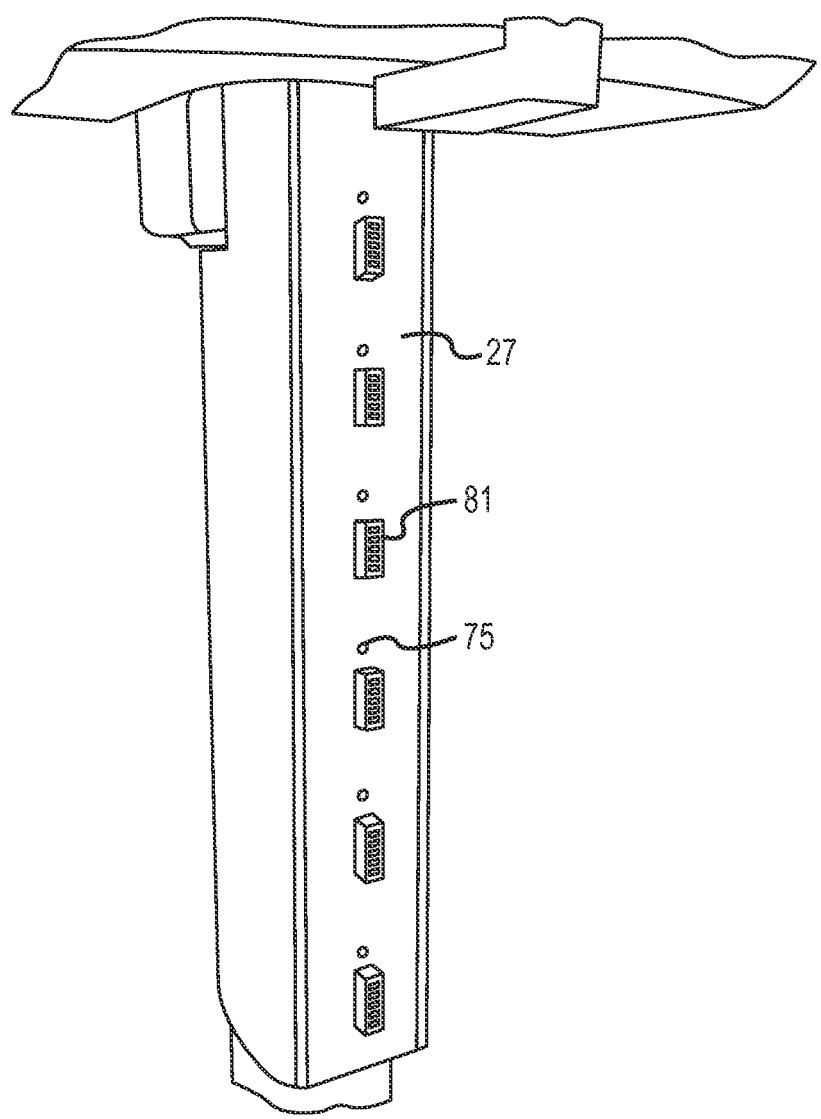

Referring now to the figures, FIGS. 1A-C illustrate a medication dispensing cart 10 (e.g., a Mobile Medication System (MMS) cart) that includes a computer/monitor 12 (also referred to herein as touch screen 12), preferably an all-in-one unit having the computing device positioned within housing 14 behind the display monitor, although other configurations (e.g., separate computing devices and monitors) could be used. FIG. 1A illustrates medication cart 10 without any cassettes 76 attached to a backplane 27 while FIG. 1B illustrates a plurality of cassettes 76 attached to backplane 27. FIG. 1C illustrates an enlarged view of backplane 27 of a medication cart 10 showing various features of the backplane. In some embodiments, computer monitor 12 comprises a touch screen display that allows a caregiver or other user to interface with the computing device and input information thereto by selecting one or more menus, inputting information, and the like via contacting monitor 12 with a finger or input device. Medication cart 10 also includes a work surface 16 comprising a slide out keyboard 18. Keyboard 18's keypad provides a second information input mechanism so that various information, such as entry of security access codes, patient related information, and the like may be input into the system. For example, medication information, caregiver ID, doses, patient information, time, date, and the like may be input into the computing system as treatments and/or medications are administered to the patient.

Work surface 16 is mounted atop post 24, which is carried in turn by a rolling base 26. Work surface 16 can optionally include holders 37 for storing items, such as antibacterial lotions, medical supplies (gloves, and the like), writing instruments, writing pads, drinks, and the like which the caregiver or user may need when administering care with medication cart 10. Medication dispensing cart 10 may include other peripheral devices, such as a barcode scanner (not shown), mouse (not shown), etc. The keyboard 18, barcode scanner, mouse, and/or other devices may be sealed to prevent the spread of infectious diseases. Medication cart 10 and/or work surface 16 may be configurable so that additional peripheral device may be connected to medication cart 10, such as a vital life sign monitor, scanner, etc.

Touch screen 12 may include a ground guard 13 to reduce or eliminate electrostatic discharge, which may shock a user of the cart 10 or damage sensitive equipment, such as the computer system or touch screen controller. Ground guard 13 may discharge electrostatic charges generated as the caregiver/user performs various duties, such as administering treatment or medications to patient located within a facility. Ground guard 13 may be positioned around an outer periphery of touch screen 12 to dissipate such charges. In some embodiments, ground guard 13 comprises a metal frame (e.g., metal strip and/or gasket) around the periphery of touch screen 12. The metal frame may be electrically grounded to medication cart 10 (e.g., an electrically conductive chassis of medication cart 10) so that electric charges are dissipated as the caregiver/user touches and interacts with monitor 12.

To further prevent damage to the computer system from static discharge, the computing device positioned within housing 14 behind the touch screen 12 may be enclosed in a protective case so that system is encapsulated and protected form any such discharge. Further, other commonly handled components, such as the keyboard 18, a mouse (not shown), a scanner (not shown), and the like may be designed to dissipate static charges as the user handles those items, such as by grounding those components with the medication cart's electrically conductive chassis.

Post 24 may be vertically adjustable so that the caregiver/user can interact comfortably with touch screen 12, cassettes 76, work surface 16, and the like from a seated or standing position and/or to accommodate caregivers/users of various height. Post 24 may be a telescoping device having an outer post member 25 that slidingly receives an inner post member 23. In an exemplary embodiment, post 24 is vertically adjustable by pressing a pivot switch 29 that electronically controls a lifting mechanism. For example, switch 29 may be electrically coupled with a power system 28 and mechanical means (not shown), such as a screw/nut drive system that utilizes a number of small ball screws, a hydraulic lifting mechanism, and the like. In operation, a user would press switch 29 to pivot the switch in one direction, such as forward, and thereby lower post 24. Likewise, the user would press switch 29 to pivot the switch in the opposite direction, such as backward, and thereby raise post 24. Power system 28 may control the vertical adjustment of post 24 via an actuator (not shown) connected to the mechanical means (not shown). In some embodiments, power system 28 includes a sensor (e.g., current sensor) connected to the actuator that may override the vertical adjustment of post 24 based on the occurrence of one or more conditions, such as the weight of an object on work surface 16 and/or the load placed upon post 24 (e.g., the weight of the cassette system and all of its contents) exceeding a defined limit. For example, if the combined weight of the work surface 16, touch screen 12, cassettes 76 and contents, and the like exceed a defined limit, the actuator will be tripped and post 24 will not be moveable upon actuation of switch 29. The sensor, or an additional sensor, may also function to disable movement of post 24 in response to sensing an obstruction that would impede vertical adjustment of the post 24, such as an object positioned above or below work surface 16. The sensed obstruction may trip the actuator by providing a measured current that indicates the obstruction. In other embodiments, post 24 may be mechanically adjusted, such as by turning a hand crank or other mechanical elevating mechanism.

In one embodiment, outer post member 25 includes the electrical backplane 27 (see FIG. 1C). Backplane 27 includes one or more ports 81 configured to receive and electronically couple with a cassette 76 (see FIG. 1B). As described below, cassette 76 may be coupled or stacked with other cassettes to form a cassette stack 30 (also referred to herein as cassette system 30) as shown in FIG. 1B. Backplane 27 may also be electronically coupled with a cassette controller unit (see FIG. 6) that controls or interfaces with the one or more plurality of cassettes 76 of cassette stack/system 30 to provide the various access controls and/or features described herein. Backplane 27 may house the cassette controller for monitoring the status and activities of cassettes 76 and/or receiving input for touch screen 12. In other embodiments, the cassette controller may be a separate unit apart from the backplane 27.

Some of the features that may be provided by the cassette controller and/or backplane 27 include: controlling the locking and unlocking of each of the bins of the individual cassettes, detecting the open/close condition of the individual bins, detecting the lock/unlock condition of the individual bins locking mechanism, automatically detecting the cassette type and configuration (e.g., detecting whether the cassette 76 is a roughly 3 inch or 6 inch cassette), automatically detecting the presence of a cassette 76 electronically coupled with (i.e., plugged into) a port 81, controlling the guiding lights, charging of the backup battery, switching the power source between the main power source (i.e., lithium ion battery, external power source, etc.) and the backup battery, controlling an alarm mechanism, interfacing with other components of the cart 10 and/or other components of other systems (e.g., central administrator), and the like.

The cassette controller and/or backplane 27 may include a storage medium (e.g., non-volatile memory, EEPROM, etc.) so that the conditions of the cart 10 and/or cassettes 76 may be monitored and recorded. For example, the cassette controller and/or backplane 27 may record and/or store information about the opening/closing of the bins, alarm conditions such as when unauthorized bin access occurs, power loss and recovery of the cart 10 occurs, and the like. This history can be provided to a central administrator, such as a central administrator 400 shown in FIGS. 6 and 7, so that the real time condition of the cart 10 and/or the history of the cart 10 can be monitored.

The cassette controller and/or backplane 27 may perform self-diagnostic tests to determine the status of the cassette controller and/or backplane 27, for example, to determine when a failure of the cassette controller and/or backplane 27 occurs. The cassette controller and/or backplane 27 may monitor the input voltage from a power source, the backup battery voltage, the cassette controller/backplane board temperature, solenoid load current, and the like. If a malfunction or other abnormality is detected, the cassette controller may report any problems to one or more systems, such as the central administrator 400, to alert the system that repairs may be needed. Cart 10 may include a status indicator (not shown) such as an indicator light (not shown) on backplane 27 and/or work surface 16 that notifies the user of a potential problem. Further, the cassette controller and/or backplane 27 may also monitor the status of cart 10 and/or cassettes 76. For example, the cassette controller and/or backplane 27 may be electronically coupled with one or more sensors (not shown) to determine if the lock mechanism is locked or unlocked, if the door is open or closed, etc. In one embodiment, the sensors respond to requests/communications received from the cassette controller and/or backplane 27. In another embodiment, the sensors provide information without receiving requests from the cassette controller, such as when the sensors sense a bin is opened and/or a locking mechanism is disengaged, etc.

For example, the cassette controller and/or backplane 27 may receive an input from a caregiver or other user to unlock one of the cassettes 76 that includes a patient's medications. The cassette controller and/or backplane 27 may instruct a locking mechanism, such as a solenoid, to unlock the requested cassette 76 and/or bin. To ensure that the locking mechanism has actually unlocked the requested cassette 76 and/or bin and that an error/failure has not occurred, the cassette controller and/or backplane 27 may be coupled with a sensor (e.g., photointerrupter sensor, etc.) and feedback loop and the status of the locking mechanism may be determined, such as if the solenoid has been disengaged. Likewise, a sensor may be used to determine if the bin door is opened or closed. In this manner, the actual status of the locking mechanism and/or bin may be determined to ensure that the actual status corresponds with what the cart's control system (and/or central administrator) believes the status to be (e.g., verifying that the bin is actually closed). The status of the locking mechanism and/or bin may be checked intermittently (e.g., at specified or irregular time intervals) or continuously. If the status of the bin is other than that expected by the cart's control system (e.g., the locking mechanism is unlocked when the control system indicates the locking mechanism as being locked), the cart's control system may be updated, the discrepancy recorded, an alarm triggered, and/or a control system (e.g., central administrator) alerted to notify one or more individuals or systems about the discrepancy. Likewise, the history of any discrepancies can be stored so that the individual carts and/or the entire cart system can be monitored and problems addressed.

As individual cassettes 76 are plugged into the ports 81, the cassette controller and/or backplane 27 may automatically detect the type of cassette that is plugged in. For example, the cassette controller and/or backplane 27 may determine if the cassette 76 is a large or small cassette (e.g., roughly 3 inch cassette, 6 inch cassette, or another size) and may automatically configure the port to interface with the cassette based on this determination, such as be installing or using the appropriate device controls/drivers, using or modifying appropriate software, and the like. In this manner, various combinations of cassette types may be used with the medication cart 10 depending on a patient's needs and/or depending on other situations. In addition, the cassette controller and/or backplane 27 may further monitor the charge of the backup battery, control the charging of the backup battery, control the guide lights, and/or control the cassette override inputs as described below.

Figure 2A:
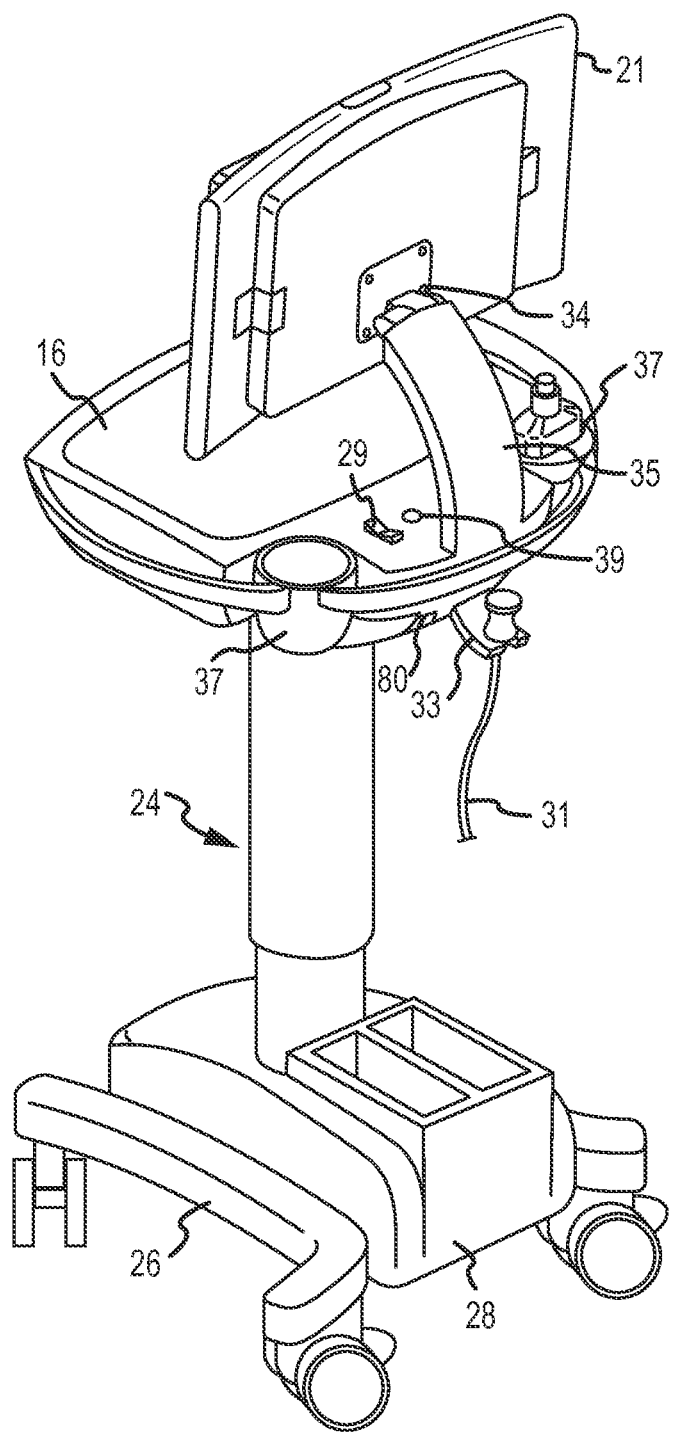
FIGS. 2A-C illustrate various rear perspective views of the medication dispensing cart of FIGS. 1A-C according to an embodiment of the invention.
Figure 2B:
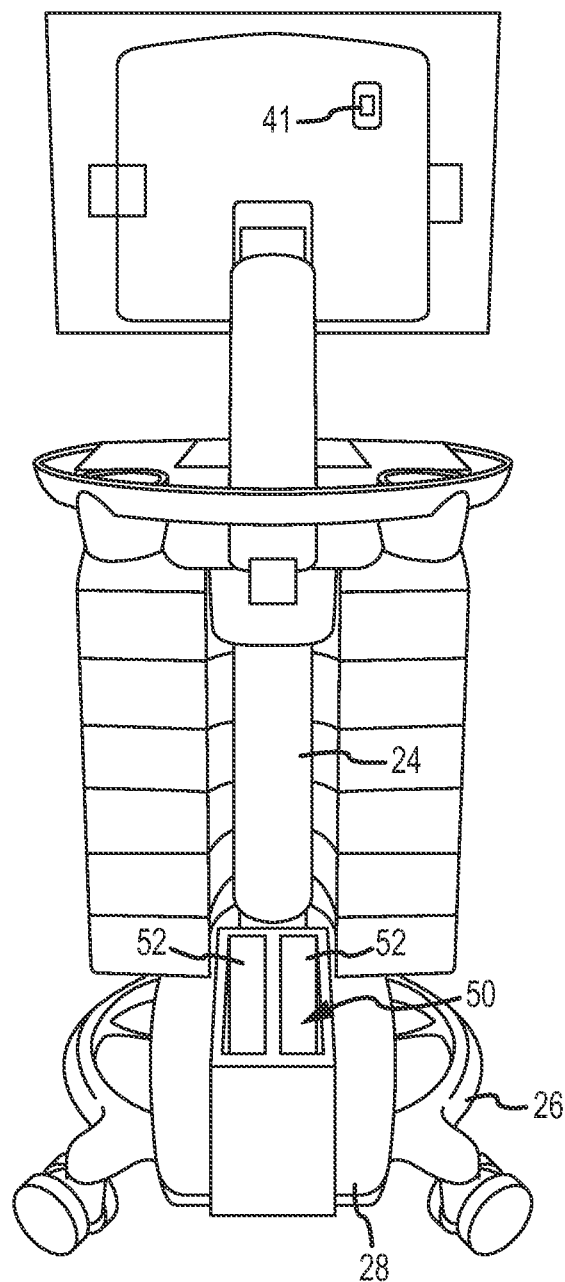
Figure 2C:
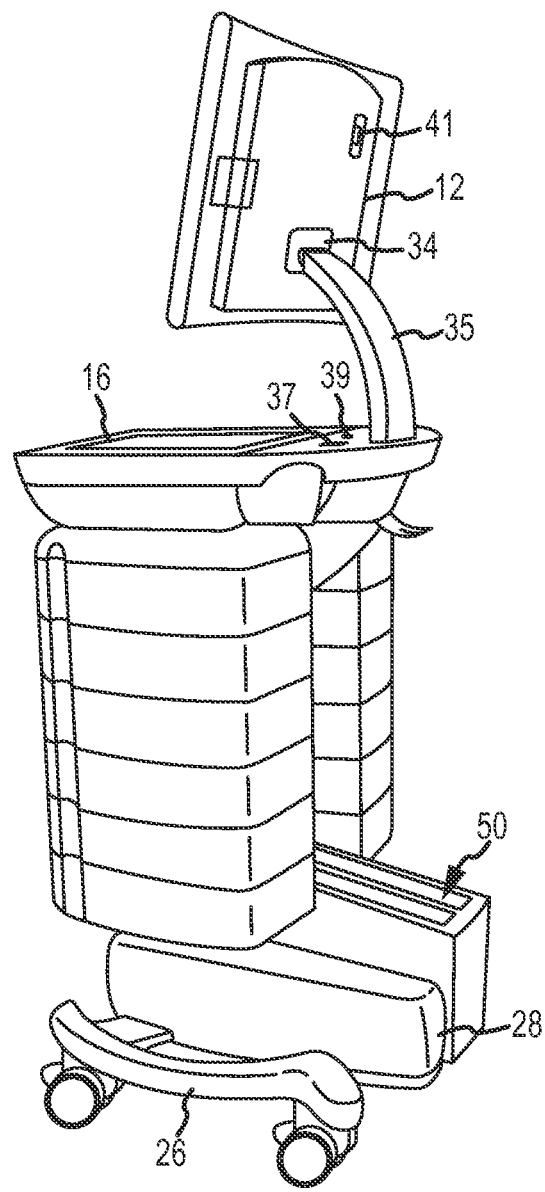

Referring now to FIGS. 2A-C, illustrated are various rear views of the present medication cart 10 showing touch screen 12, work surface 16, post 24, and power system 28, which is supported by rolling base 26. Work surface 16 can further include hidden USB port 80 for use if additional electronic devices need to be employed, such as scanners, vital sign monitors, mouse devices, and the like. Touch screen 12 may be attached to post 24 or the rear surface of work surface 16 via mount 35 to maximize the usable area of work surface 16 (i.e., provide the maximum work space to the caregiver/user). Touch screen 12 may be mounted using a tiltable bracket 34 so that the viewing angle of touch screen 12 can be adjusted to accommodate the caregiver/user. A clear hard covering may be applied over the monitor portion of computer/monitor 12 in order to make computer/monitor less susceptible to scratches and impact. The covering may be about an $1/8^{th}$ inch thick and made of acrylic polymeric plastic or other suitable plastic polymer.

Work surface 16 may include a standby button 39 (e.g., a HIPAA (Health Insurance Portability and Accountability Act) button) that may be used to quickly place touch screen 12 into a standby or disabled mode so as to protect sensitive information that may be displayed on touch screen 12. For example, touch screen 12 may display patient information, which may include sensitive information such as medical history, prescribed medications, and/or other personal information. If the medication cart 10 is in a public area, such as when the cart is being moved between patient rooms, standby button 39 may be pressed to override the input signals from the computer system and black out touch screen 12. Standby button 39 may include a standby indicator that visually displays the standby status of the standby button and touch screen 12, such as to display whether the monitor is in standby or disabled mode. The standby indicator may be color coordinated to display the status of the standby button and/or touch screen 12. For example, standby button 39 may be green when touch screen 12 is not in standby or disabled mode and red when touch screen 12 is in standby or disabled mode.

When touch screen 12 is in standby or disabled mode, touch screen 12 may not display anything (e.g., screen is black) so that the monitor and/or computer system appears to be off. In other embodiments, the standby or disabled mode may generate a screen saver image or series of images/videos that are displayed. Providing a standby indicator allows a caregiver or other user to quickly determine whether the screen is blank or in screen save mode due to touch screen 12 being in standby or disabled mode or being powered off. In this manner, accidental restarts may be avoided that may otherwise occur due to a caregiver/user mistakenly powering off cart 10's computer system's when touch screen 12 does not respond to inputs from a mouse, keyboard, or touch screen input. Avoiding accidental restarts may avoid deletion of material entered into, but not yet stored in, the computer system and/or may avoid other problems associated with not realizing that touch screen 12 is in standby or disabled mode (e.g., interruption of data continuity, mistaken belief that cart 10 is malfunctioning, etc).

In some embodiments, cart 10's computer system may automatically switch touch screen 12 to standby or disabled mode after a predefined time has elapsed without input from the caregiver/user to conserve battery power and/or protect sensitive information. The standby button's 39 indicator may display when the monitor 12 is in such standby or disabled mode.

Power system 28 may include a battery receptacle 50 having one or more slots 52 (element 302 of FIGS. 3A-D) that are configured to receive a battery. Power system 28 may be placed near the bottom of medication cart 10 to lower the cart 10's center of gravity and provide stability to the cart. Additional aspects of power system 28 are illustrated in FIGS. 3-4.

Referring now to FIGS. 3A-D, power system 28, which is connected through post 24 to touch screen 12, includes a power system controller (not shown, but see FIG. 6) and a plurality of battery slots 302 that are configured to receive a battery 402 (see FIG. 4). Power system 28 is coupled with and supported by rolling base 26. Power system 28 may be detachably coupled with an external power supply, such as through a detachable power cord 322. Power system 28 may include a universal AC power input so that the power cord 322 may be swapped to match the AC plug, thereby allowing the medication cart to be used in virtually any country. Power system 28 may power medication cart 10 via the external power supply (i.e., without a battery) and/or may charge batteries 402 when connected with the external power supply. Power system 28 may further include a power supply bracket 326 to secure the external power supply (e.g., power cord 322) to the power system 28.

Battery slots 302 may each slidably receive a battery 402. Disposed toward a bottom surface of battery slots 302 may be one or more ports, 306 and 308, that electrically couple or plug into corresponding connectors on the battery (see FIG. 4). Ports, 306 and 308, may each be a five-pin electrical connector configured to support and/or operate with hot swappable smart Li-polymer battery packs. In one embodiment, port 306 may be a power connection port that draws power from the battery 402 during operation of medication cart 10 and/or provides power to the battery 402 when an external power supply is plugged into the power system 28. In this manner, power system 28 may recharge battery(s) 402 plugged into power system 28. In some embodiments, port 308 may be a System Management Bus (SMB) port. The SMB port 308 may allow the power system controller to communicate with the battery during use and/or charging. For example, through SMB port 308 and/or power connection port 306, the power system controller can communicate with the battery to monitor and track usage and/or charging of the battery and thereby maximize the lifespan and/or potential of the battery.

For example, the power system controller can receive information from the battery such as an optimal charge current and/or charge voltage and vary either or both the charge current or voltage during a charge cycle. Similarly, the power system controller can receive information from the battery about an optimal discharge current and/or discharge voltage during operation of the cart 10 and adjust the cart's power settings and battery usage accordingly. As the battery is charged and/or ages during use, the charge and/or usage requirements of the battery may change. This information (i.e., the changed charge and/or usage information) may be provided to the power system controller from the battery so that the charge setting (i.e., current and/or voltage) and/or usage settings (i.e., charge and/or voltage supplied from each battery) may be adjusted in real time, and thereby optimize the charge and/or usage of the battery. In this manner, the charge and/or operation of each battery may be monitored by the power system controller. Other features that the power system controller and/or battery can monitor and/or control include: The battery cell voltages, battery pack voltages, charge current, discharge current, charging temperature, discharging temperature, idle mode temperature, and the like. The communication between the battery and the power system controller allows the medication cart to accommodate and adjust to different batteries so that battery usage and/or charging is optimized regardless of the batteries used. Further, this information may be monitored and provided to a central administrator 400 so that battery performance and/or cart performance may be monitored.

If the stress levels of the battery (i.e., the operational temperature, voltage, current, etc.) exceed pre-defined parameters, the power control system may disconnect the battery from use and/or charging and alert one or more other systems, such as a central administrator 400 and/or the cart's monitor/computer controller. For example, the battery may communicate to the power system controller (via SMB port 308) that the current and/or voltage of a charge exceeds a safe amount (or is excessive for optimal charging). Upon receiving such a request, the power system controller can adjust the current and/or voltage provided or disconnect the battery from charging so as to avoid malfunctioning or failure of the battery. In some embodiments, the power system controller, and/or the battery itself, can reset the battery after the stress condition is cleared. By monitoring the condition of the battery(s) and adjusting the charging and/or operational demands accordingly, the power control system may avoid catastrophic failure of the battery and, thus, failure of the medication cart 10. As explained below, if the power system controller is unresponsive to requests from the battery (e.g., a request to adjust the current and/or voltage), the battery itself may disconnect from the power system to avoid malfunctioning or failure. The power system controller and battery may function in a similar manner during operation so as to adjust the power requirements demanded of the battery and/or disconnect the battery from power system 28.

Further, the power system controller may record historical data about each of the batteries used. This data may be used for debugging or monitoring purposes, such as to determine when a battery needs replacement or to determine an optimal arrangement for the batteries within a fleet of medication carts. This historical data may be provided and/or stored by the central administrator. The historical/lifetime data for each battery may include: maximum/minimum temperature, maximum/minimum cell voltage, maximum/minimum pack voltage, maximum charge current, maximum discharge current, maximum charge power, maximum discharge power, life maximum average discharge current, life maximum average discharge power, average temperature, etc.

Each battery may include a unique serial number that is read by the power system controller and/or provided by the battery so that the data (i.e., real time and/or historical) for each battery may be recorded and monitored regardless of whether the battery is used with the same medication cart 10 or different medication carts. In other words, the power system controller is able to recognize each battery that is used with the medication cart and provide battery data to central administrator 400 that corresponds with the specific battery used. In this way, the central administrator may keep a database of each battery used in the system. The database may include an identifier for each cart the batteries were used with, the performance of each battery over their lifetime, and/or the real time status of each battery.

Figure 3A:
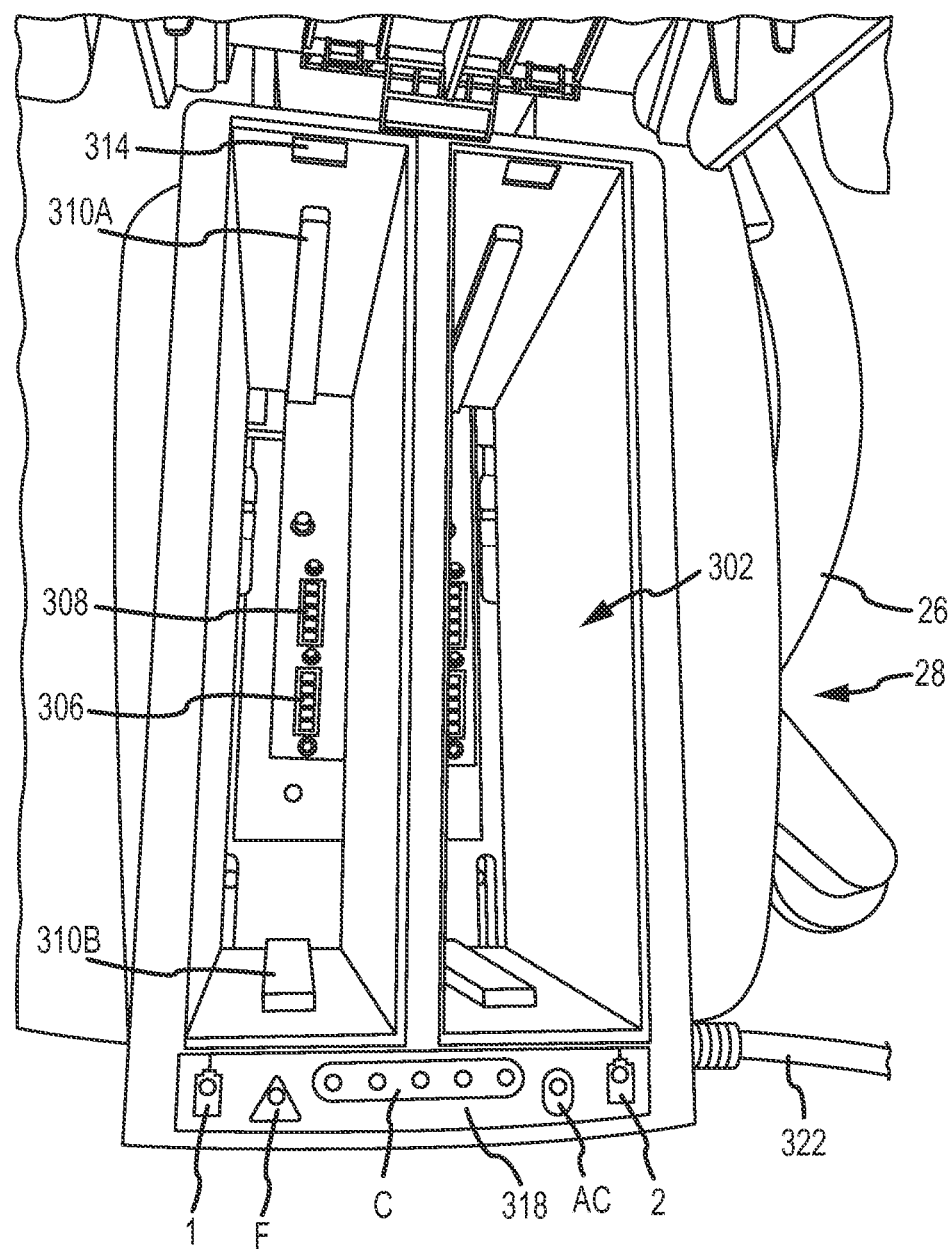
FIGS. 3A-D illustrate various perspective views of a power system for the medication dispensing cart of FIGS. 1A-C according to an embodiment of the invention.
Figure 3B:
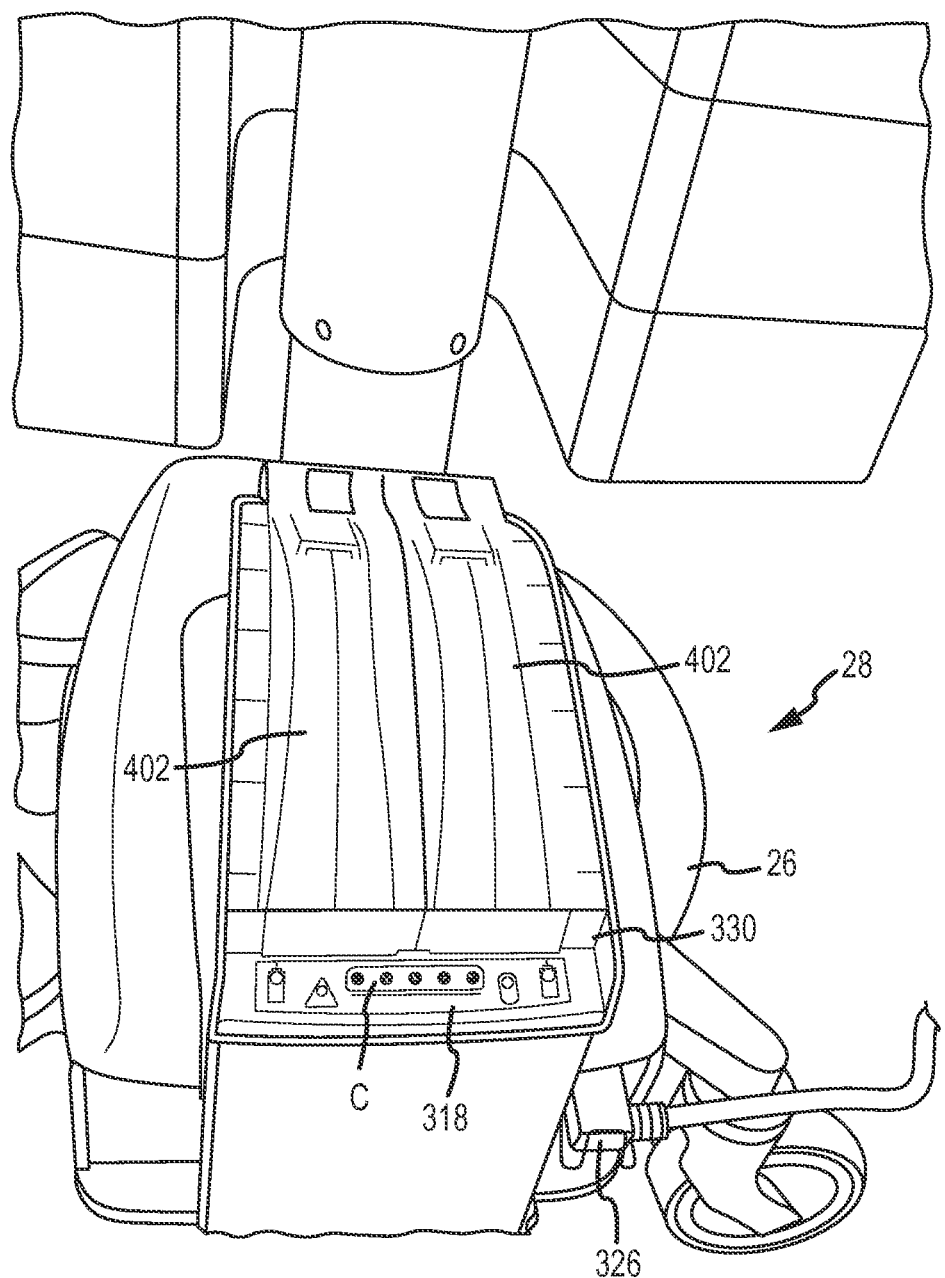

Power system 28 may include hot swappable dual battery slots 302, or put another way, the battery slots 302 may be hot swappable. Hot swappable battery slots 302 may allow for a battery to be removed from power system 28 without interrupting the power provided to the medication cart 10 (e.g., without loss of power, or data, to computer/monitor 12). FIG. 3D illustrates power system 28 having a single battery 402 inserted within one of two battery slots 302. The single battery 402 is able to provide sufficient power to operate medication cart 10. Medication cart 10 may automatically adjust to draw power from one of the batteries as the other battery is detached and removed from one of the battery slots 302. Individual batteries 402 may be removed from power system 28 to charge the battery, replace the battery, inspect the battery, perform maintenance, and the like. Further, because an individual battery 402 is capable of powering medication cart 10, the medication cart is not susceptible to failure due to the failure of a single battery. In other words, each battery 402 may act as a backup power supply in case of failure of the other battery. Further, the hot swappable feature of the power system 28 provides for continuous operability of the medication cart 10 without having to plug in the medication cart to recharge the batteries. For example, the medication cart could essentially run indefinitely without plugging the medication into an external power source, provided the batteries are regularly removed and/or recharged.

The power system controller may communicate status information about the battery to power system 28, which information may be visually displayed via one or more displays 318 (e.g., LED indicators) of power system 28. For example, FIG. 3A illustrates display 318 comprising the following indicators: an external power supply indicator AC that shows when an external power supply is plugged into power system 28, a fault indicator F that displays when a battery is malfunctioning or otherwise has a problem, an indicator for one or more battery slots 302 that shows when a battery is connected with each slot (e.g., indicators 1 and 2), and a charge level indicator C that shows the charge level of a selected battery or the charge level of the power system. The charge level of each battery may be displayed via indicator C by selecting either indicator 1 or 2, otherwise indicator C may display the overall power level of power system 28. In this manner, the caregiver/medication cart user may quickly determine the real time status of each battery being used for power system 28 or determine the overall power level for power system 28.

Figure 3C:
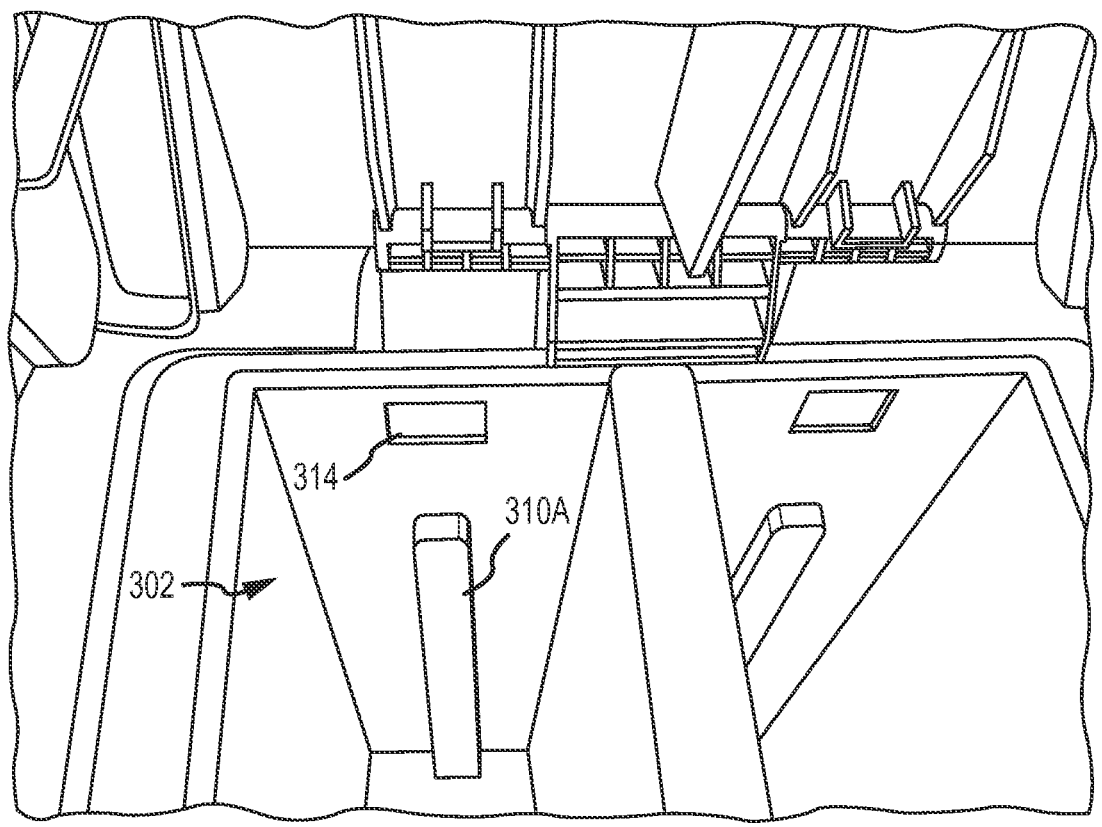
Figure 3D:
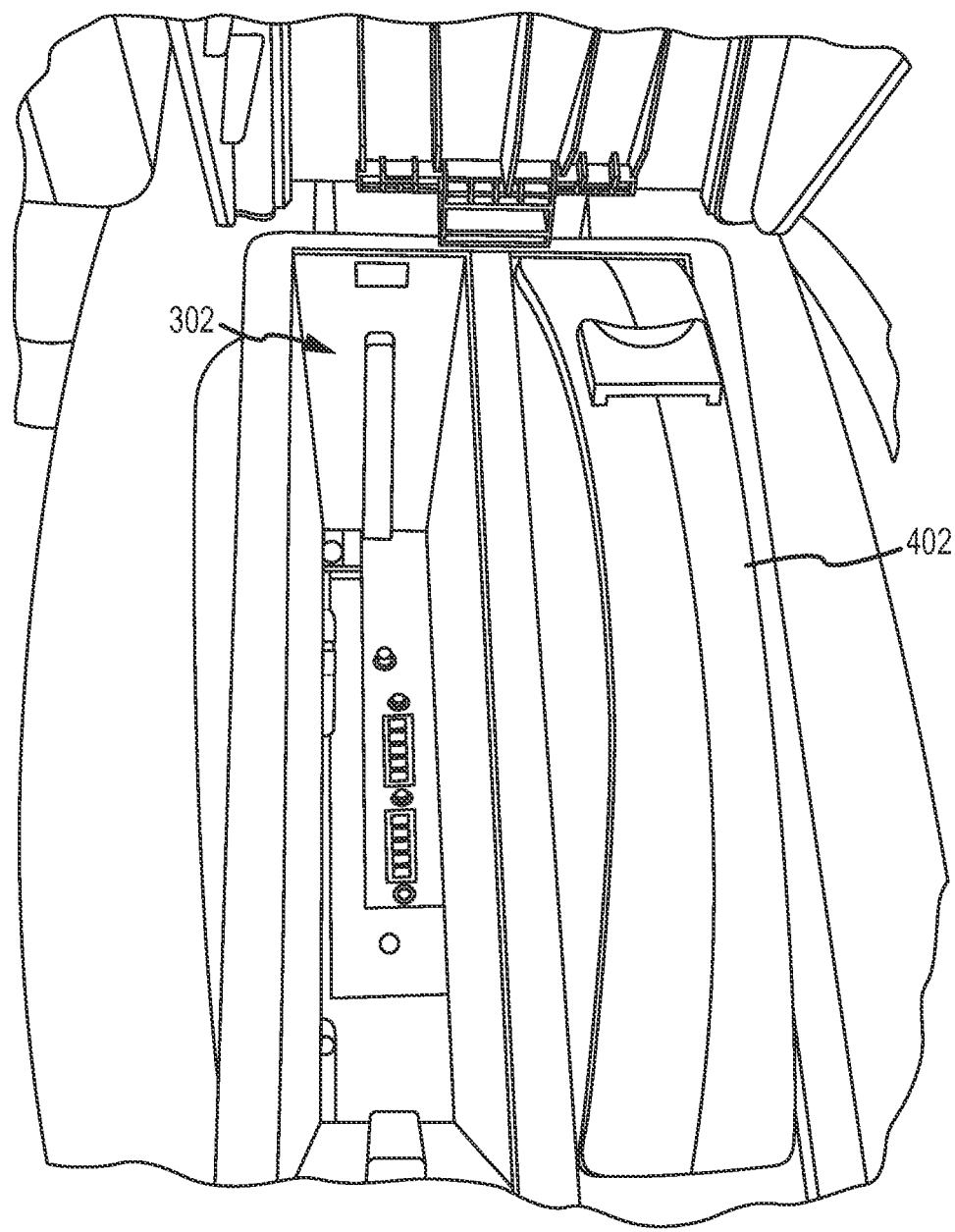

Each battery slot 302 may additionally include a receiving mechanism that facilitates in receiving battery 402 into the slot (see FIG. 3C). For example, power system 28 may include a first slide member 310A and a second slide member 310B that correspond with slide guides (see FIG. 4) on the battery to facilitate in slidably receiving battery 402 within battery slot 302. The first slide member 310A and second slide member 310B may be sized and/or shaped differently so as to properly orient battery 402 upon insertion into the slot 302. In other words, the slide members may be shaped and/or sized so that battery 402 is only receivable in one orientation (i.e., the battery only fits into the slot in one direction).

Each slot 302 may further include a latching mechanism 314 that detachably couples the battery in the slot 302. The latching mechanism 314 may be a recessed portion in the slot that is configured to receive a latch or hook (see FIG. 4) of battery 402. Other forms of detachably coupling the battery are also contemplated herein, which may include detents, grooves and corresponding members or gaskets, coupling cam mechanisms, locks, pins, screws, and the like. The latching mechanism may allow for quick release of the battery from within the slot so that a user may quickly exchange batteries in one or more of the slots with a single hand. For example, the user may grasp the battery with one hand and engage a removal member with a finger or thumb to unlock the battery within the slot.

Power system 28 may further include a lid 330 (see FIG. 3B) that is pivotally coupled with power system 28 to enclose and/or secure the batteries within slots 302. FIG. 3B illustrates the power system 28 including two batteries 402 coupled within battery slots 302 with the lid 330 enclosing the batteries within the power system. The figure further shows displays 318 indicating a full charge level C for power system 28 and/or for one of the selected batteries.

Figure 4A:
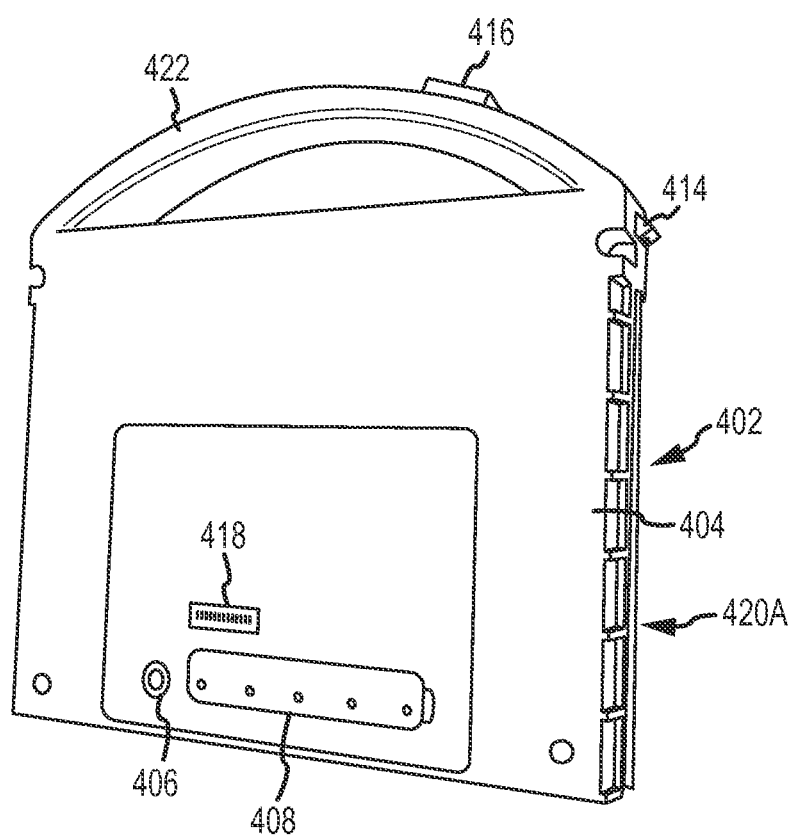
FIGS. 4A-B illustrate various perspective views of a battery that may be used with the power system of FIGS. 3A-D according to an embodiment of the invention.
Figure 4B:
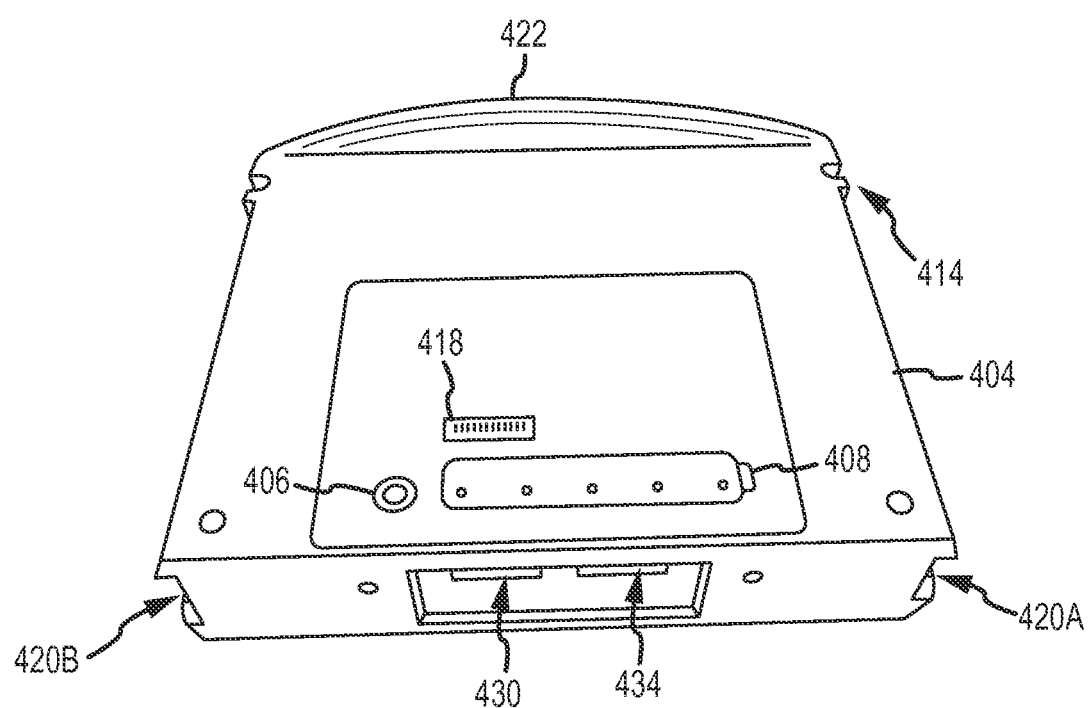

Referring now to FIGS. 4A-B, illustrated is a battery 402 that may be used with power system 28. Battery 402 may be a hot swappable smart Li-polymer battery pack (Lithium ion battery). The Li-polymer battery pack may provide a longer battery life, higher energy content per weight, and substantially no periodic maintenance charge when compared to similar lead-acid batteries. In one embodiment, each battery pack provides a voltage range of 13.0 to 16.4 volts, and preferably in the range of 14.8 volts.

As discussed, battery 402 can be charged in combination with cart 10 or independently of cart 10. Work surface 16 may include a plug rest 33 (shown in FIG. 2) for conveniently storing the power cord 322 when the cart 10 is being moved, operated solely on battery power, or not in the vicinity of a power source. Each individual battery 402 may be designed to power cart 10 through at least one eight hour shift before requiring recharging, and preferably through at least one 10 hour shift. In other words, each battery 402 may power medication cart 10 for at least a single 8-10 hour shift. This operational time of a single battery may allow the other battery to be removed for recharging, inspecting, maintenance, and the like. When two batteries are used the operational time can be extended to last beyond two shifts, or approximately 18-20 hours.

Battery 402 may include one or more connectors, 430 and 434, that allow the battery to communicate information to an external source, such as the power system controller and/or an external battery charger. Connector 430 may be a power connector that corresponds with port 306 in power system 28 to provide power to power system 28 and/or receive power from an external source. Likewise, connector 434 may be a SMB connector that corresponds with SMB port 308 in power system 28. The battery 402 may additionally include an internal interface board (not shown) that monitors the characteristics described above (e.g., charge, voltage current, temperature, etc) and communicates this information to the external source. External communication from the interface board may be provided via SMB connector 434 and/or power connector 430. For example, during charging, the interface board may initially provide, via SMB connector 434, information to an external battery charger or the power system controller regarding an optimal charge current and/or voltage, which current and/or voltage the battery charger and/or power system controller may provide. As the battery charges, the optimal charge current and/or voltage may change, which may be detected by the interface board and relayed to the battery charger and/or power system controller. Similarly, the interface board may itself monitor the current and/or voltage provided by battery 402 during operation of the cart 10 and relay this information to the power system controller. The interface board may also monitor the current and/or voltage provided from or received by the power connector 430 and provide this information to an external source.

As described above, battery 402 may include several layers of protection to protect against malfunction and/or catastrophic failure, which may damage the medication cart 10 and/or cart's control system. For example, the interface board may detect when stress levels (e.g., temperature, current, voltage, etc.) exceed predefined parameters. In such instances, the board may relay this information, via SMB connector 434, to an external source (e.g., the power system controller and/or battery charger) so that one or more adjustments may be made and/or the battery may disconnect itself from the external source. Further, battery 402 may reset itself once the stress condition is cleared or otherwise taken care of.

Battery 402 may utilize gas gauging technology, such as Texas Instrument Impedance Track® (TI bq20z90 IC), to generate accurate readings of the battery's remaining capacity. The battery may support the Smart Battery Specification (SBS) v1.1 (i.e., may be SBS v1.1 compliant) or other standards. Battery 402 may include one or more displays 408 that indicate the status of the battery, such as the charge level. To show the status (e.g., charge level), battery 402 may include a battery status button 406, which, when pressed, provides an status indication via display 408, such as illuminating one or more LEDs. The battery's case 404 may be constructed of a flame retardant plastic. The case may be ultrasonically welded together and/or comprise one or more screws to fasten the case together. The battery may also comprise a unique serial identifier that identifies the individual battery. The information associated with the unique serial identifier may be stored internally in one or more storage mediums. This unique identifier may also be provided to an external source via SMB connecter when the battery is coupled with the external source, such as a battery charger or power system 28.

The battery's case 404 may include slide guides 420A & B disposed on opposite sides of the case that correspond with slide members 310A & B, respectively. The slide guides 420A & B may be shaped and/or sized so that each slide guide corresponds only with one of slide members 310A & B to ensure that the battery is properly oriented when it is inserted into slot 302. The battery may further include a handle 422 so that the battery 402 may be easily transported and may additionally include a locking mechanism (see FIG. 4A), such as latch 414 that is configured to lock into recess portion 314 of power system 28. As the battery 402 is slid into slot 302, the latch 414 may retract into handle 422 until the battery is fully positioned within slot 302. Afterwhich, latch 414 may lock into recess 314, such as by being outwardly biased via a spring (not shown) disposed within handle 422. Latch 414 may be coupled with a removal member, such as knob 416, that retracts latch 414 within handle 422 when engaged (e.g., when slid along handle 422). In this manner a user may easily remove the battery by grasping handle 422 and engaging knob 416, which retracts latch 414 within the handle, thereby unlocking the battery 402 and allowing the battery to be removed from slot 302. As described above, battery 402 may include other locking mechanisms, which may include detents, pins, compliant members, locking cams, screws, etc.

Medication cart 10 may also include a backup battery (not shown) that provides some cart functionality in case of a complete power failure of battery(s) 402. The backup battery may be a lead-acid battery or a Li-polymer battery. The backup battery may allow medication cart 10 to remain operational for a short period of time so that one or more operations may be completed, such as administering medications, providing treatment, locking and securing narcotics within cart 10, entering patient or treatment information into cart 10's computer system, and the like. Further, the backup battery may be electrically coupled with the cassette controller and/or backplane 27 to provide complete access to all the cassettes 76 in case of a complete power failure. Complete access to all the cassettes 76 in the event of a complete power failure may be provided upon providing one or more inputs, such as by engaging an administrator key and one other key (e.g., nurse key). Upon providing the inputs (e.g., administrator and nurse key), the backup battery may override the system control locks and provide access to any or all the cassettes 76. In this manner, any or all cassettes 76 may be accessed even when the cart's control system is non-operational, thereby allowing access to medication and/or personal possessions that may be kept in the cassette (i.e., in one of the cassette's bins). In addition, the power system controller may control the charging of the backup battery to ensure that the backup battery is charged in case of a complete power failure.

Figure 5A:
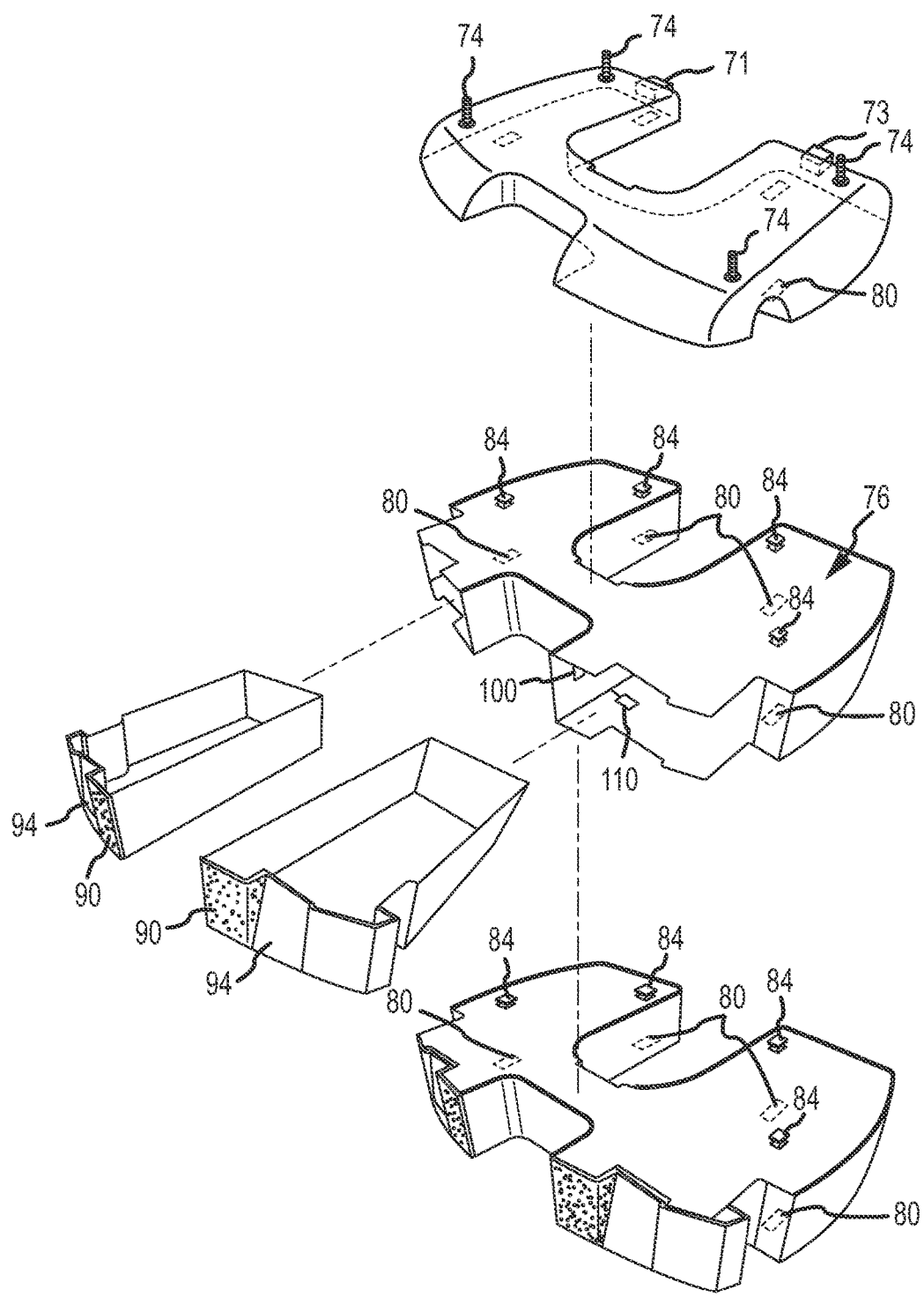
FIGS. 5A-D illustrate various views of a cassette system and individual cassettes of the medication dispensing cart of FIGS. 1A-C according to an embodiment of the invention.
Figure 5B:
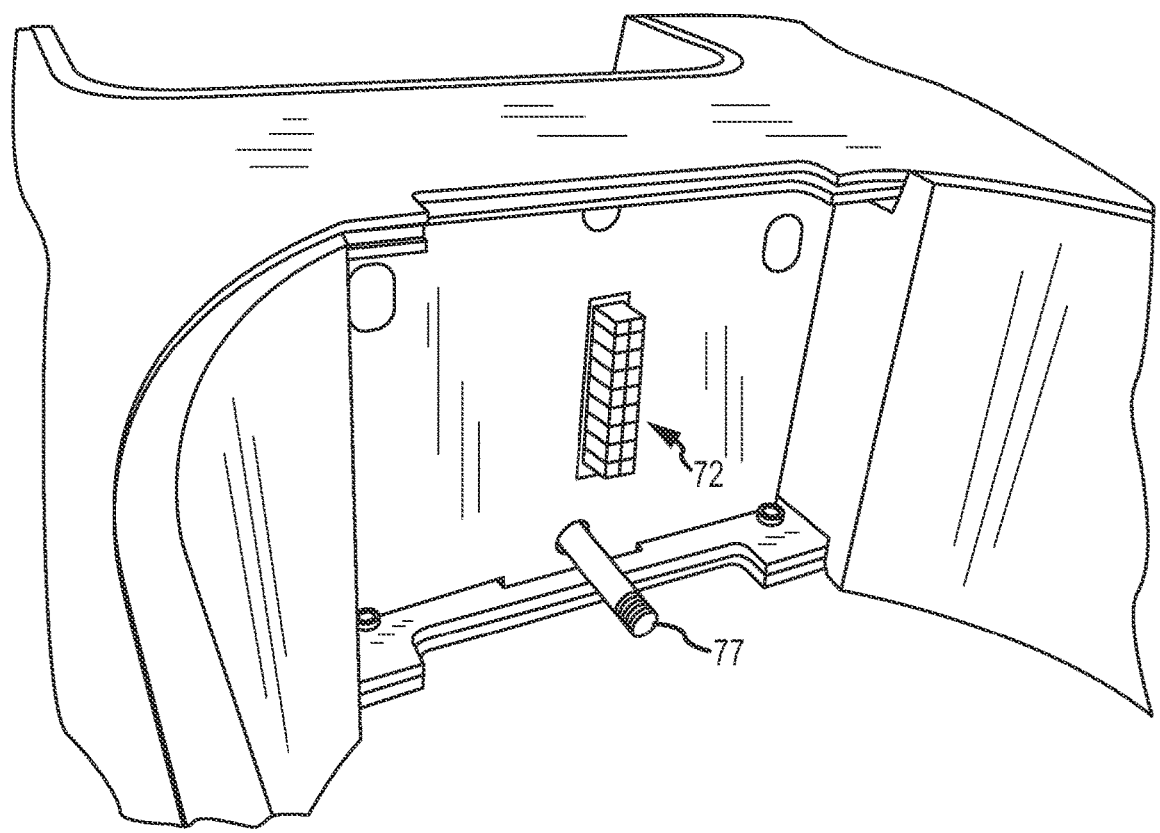
Figure 5C:
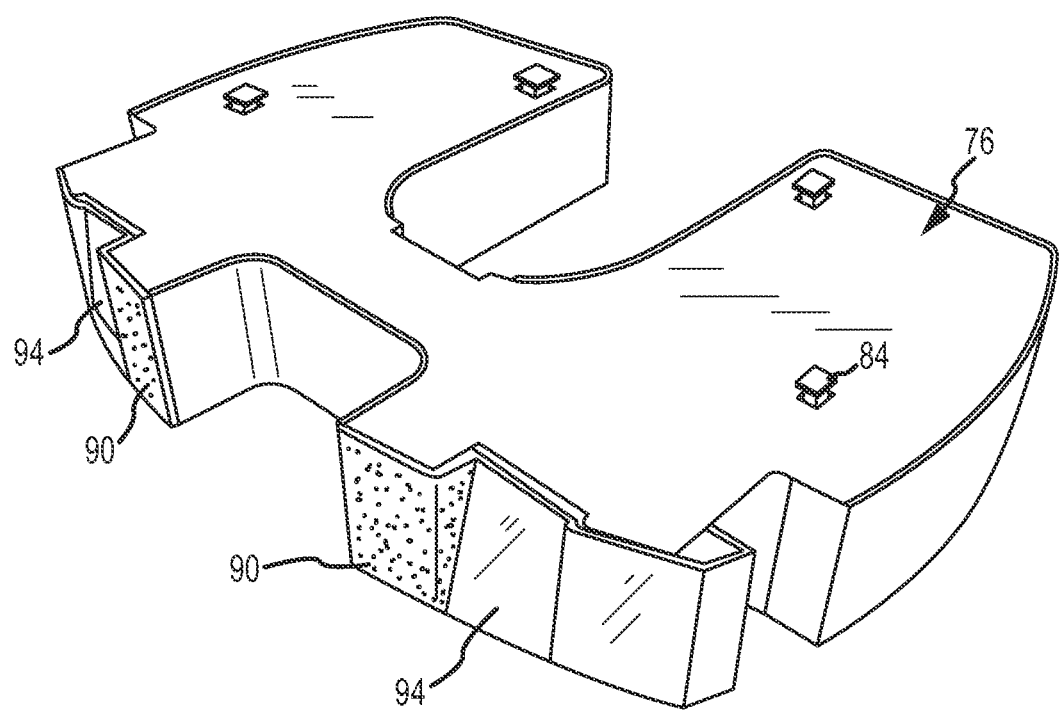
Figure 5D:
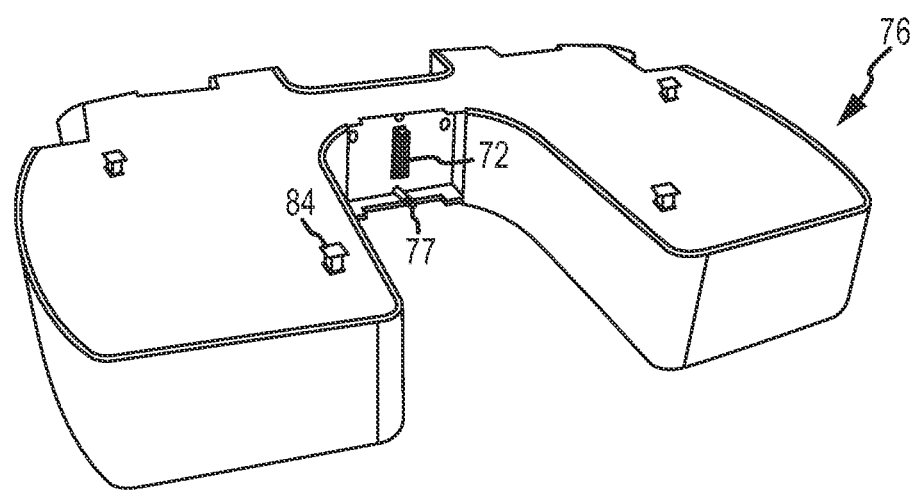

Referring now to FIGS. 5A-D, FIG. 5A illustrates an exploded, detailed view of the cassette system 30. FIGS. 5B-D illustrate an individual cassette 76 of the cassette system 30. Cassette system 30 is preferably modularized, and includes a cassette manager 70. The cassette system 30 is generally connected to work surface 16 and wired to touch screen 12 via backplane 27. More particularly, the top of cassette manager 70 may be fastened to the under surface of work surface 16. Accordingly, cassette manager 70 includes fasteners 74 (e.g., bolts) along its top surface that allow cassette manager 70 to be bolted to the under surface of work surface 16. Optionally, cassette manager 70 includes a first key override lock 71 and a second key override lock 73 that may be operable with the battery backup (not shown) as described above to provide access to any or all the cassettes and/or bins in case of a complete power failure or for any other reason.

Beneath cassette manager 70, at least one cassette 76 is latched. As briefly described above, cassettes 76 may vary in size. In one embodiment, the cassettes may range in size between about 4 and 8 inches in height (and preferably about 6 inches) and/or about 2 and 4 inches in height (and preferably about 3 inches), although a variety of sizes are contemplated herein. Cassette system 30 may include any combination of sized cassettes 76. In one embodiment, if cassette system 30 includes all large sized cassettes (e.g., 4-8 inch cassettes), up to 6 cassettes may be included in cassette system 30. In another embodiment, if cassette system 30 includes all small sized cassettes (e.g., 2-4 inch cassettes), up to 12 cassettes may be included in cassette system 30. In still other embodiments, cassette system 30 may include any combination of large and small sized cassettes so that more or less cassettes may be added (i.e., 8 cassettes, 10 cassettes, etc.). As soon as a cassette 76 is added, it may be sensed or identified by backplane 27 and/or the cassette controller and may not be opened except by a user with an authorizing pass code. As described above, backplane 27 may automatically configure itself to operate with the various sized cassettes and cassette configurations.

FIGS. 5B and 5D illustrate cassette 76's connector 72 that couples with port 81 on the backplane 27. Connector 72 may communicatively couple the cassette system controller or backplane 27 (or cart 10's computer system) with cassette 76 so that the various cassette functionalities described herein may be provided, such as: locking and unlocking cassette bins, illuminating the guide lights, assigning cassette bins as patient specific or utility specific bins, sensing the lock/unlock status of bins, sensing whether the bins are open or closed, and the like. Cassette 76 may further include a post 77 that corresponds with an aperture (see FIG. 1C, element 75) on backplane 27. Post 77 may facilitate in properly aligning cassette 76 with backplane 27 to ensure that connector 72 easily plugs into the port 81. When cassette 76 is plugged into backplane 27, the cassette controller unit may sense the size of the cassette (i.e., sense whether the cassette is roughly 6 inch or roughly 3 inch cassette as described herein), and may further sense the cassette 76 configuration of cassette system 30. Backplane 27 may also sense additional information associated with cassette 76, such as whether one or both of the bins are designated as patient specific or utility bins. Patient specific bins may be bins that have been assigned for use in storing personal belongings of the patient and/or medication specifically prescribed for the patient and/or specifically for use for the patient. Utility bins may be bins that have been assigned to carry common items used by caregivers or other users as they assist the patients (e.g., bandages, gauze pads, syringes, over the counter medications, etc). Utility bins may automatically open upon receiving an authentication of the caregiver or user or may not require any authentication to open. The cassettes and/or bins may be re-assignable by the nurse and/or central administrator. In some embodiments, cart 10 may include all utility bins and/or cassettes, all patient specific bins and/or cassettes, or any combination thereof.

Each cassette 76 (and cassette manager 70) may include a latching mechanism. The latching mechanism may include a plurality of dovetail-shaped cutout portions 80 that are dimensioned to receive dovetail-shaped projections 84 of an adjacent cassette 76. Dovetail shape projections 84 may be positioned on the top surface of the cassette 76, while the dovetail shaped cutouts are positioned on the bottom surface of the cassette 76. Similarly, cassette manager 70 may include a plurality of dovetail-shaped cutout portions 80 on its bottom surface so that cassette manager 70 may couple with a cassette 76 positioned immediately below cassette manager 70. In operation, dovetail projections 84 may simply slide into dovetail cutouts 80.

As illustrated, cassette manager 70 and cassette 76 are generally U-shaped to facilitate engagement with post 24 by fitting around post 24. The U-Shaped cut out portion of cassette 76 and/or cassette manager 70 may include a flat portion that includes connector 72 and post 77. The flat portion may correspond with the flat backplane 27. Each cassette 76 typically has at least two bins 94 that are independently lockable through electronic locks 100 and that have corresponding sensors 110. Sensors 110 determine if a bin 94 is open or closed and or may determine if the electronic lock 100 is engaged or disengaged as described above. Also, as described above, the cassette controller and/or backplane 27 may continually monitor the status of the bins 94 so that upon unauthorized access, an alarm is sounded and an email is sent to a system administrator (e.g., central administrator). In some embodiments, all or a majority of locks 100 are software controlled, while in other embodiments, locks 100 may use keys or a combination of keys and software lock. For example, lock 100 could include a software controlled solenoid actuator connected to a lever.

Cart 10's computer system (e.g., touch screen 12) can be programmed to lock and secure every bin 94 unless and until unlocked by an authorized user having an appropriate level of authorization who inputs a correct security code via keyboard 18, touch screen 12, a scanner (e.g., bar code scanner), and the like. The cassette controller may have a time out feature so that all cassettes and/or bins are locked if an input is not received from a caregiver or other user within a defined time period, for example, if a bin 94 is not opened within a predefined time after being unlocked.

In another embodiment, cart 10's computer system (e.g., touch screen 12) may provide access to a patients bin 94 upon a positive verification of the patient, such as by scanning a patient's wristband. Access to the bin 94 may also require two positive identifications of the patient, such as by scanning the patients' wristband and receiving a confirmation of a secondary identifier from the caregiver or user that the patient identified by the system is in fact the patient being treated. The confirmation (i.e., secondary identifier) may include receiving an input from the caregiver via the touch screen, keyboard, mouse, and the like acknowledging that the patient's characteristics displayed on touch screen 12 (e.g., patient's sex, height, weight, name, age, hair color, etc.) match the actual patient receiving care. Upon receiving the secondary identifier and/or providing cassette 76 access based on authorizing the patient, guide lights 90 for the patient's bin 94 may be illuminated to visually guide the caregiver to where the patient's bin is located.

Access to a bin 94 containing narcotics may require two pass codes; otherwise one pass code may unlock a bin 94. Each user (e.g., a nurse) may have his or her own pass code or codes so that cart 10's computer system identifies each user who accesses each bin 94 by the pass code used. Likewise, cart 10's computer system may record the time and date of the access by that user. This access information (e.g., date, time, user, etc.) may be reported to the central administrator 400 (see FIG. 6) so that bin access may be monitored. Central administrator 400 may network a plurality of medication carts 10 so that a nurse's identifier and/or password is capable of unlocking and operating any medication cart 10 networked to the central administrator 400.

Cart 10 may be optionally provided with a plug-in scanner for reading medication containers to facilitate in accurately loading cassettes 76/bins 94 and/or providing cart 10's computer system (or central administrator 400) with information about the medications being loaded into each bin 94. In this way, the system administrator (e.g., central administrator 400) can have a real time inventory of medications in all carts in its system, knowing exactly what type and how much medication is in each bin 94 of each cart.

As described above, each cassette 76 may include one or more guiding lights 90 that illuminate (e.g., the exemplary illumination region shown in cross hatch in FIG. 5A) a portion or the entire face of bin 94 to visually display a bin 94 having a needed medical supply and/or corresponding to an identified patient. For example, when a nurse provides an authorization code to access a patient's bin 94, the guide light 90 may illuminate the inner third of the face of the bin 94 (e.g., illuminate a third of the bin closest to the post) so that the nurse may quickly identify which bin is the patient's bin that has been unlocked. In some instances, more than one bin 94 may be assigned to a patient so that upon entry of an authorization code and selection of that patient, the face of multiple bins illuminate. Similarly, guide lights 90 may illuminate a specific one of the patient's bins 94 based on a selection of a drug to administer to the patient that the system recognizes is kept in the specific bin. In this manner, the system may differentiate between multiple bins 94 assigned to a specific patient. Likewise, the system may illuminate guide lights 90 of a utility bin when general medications are required.

Figure 6:
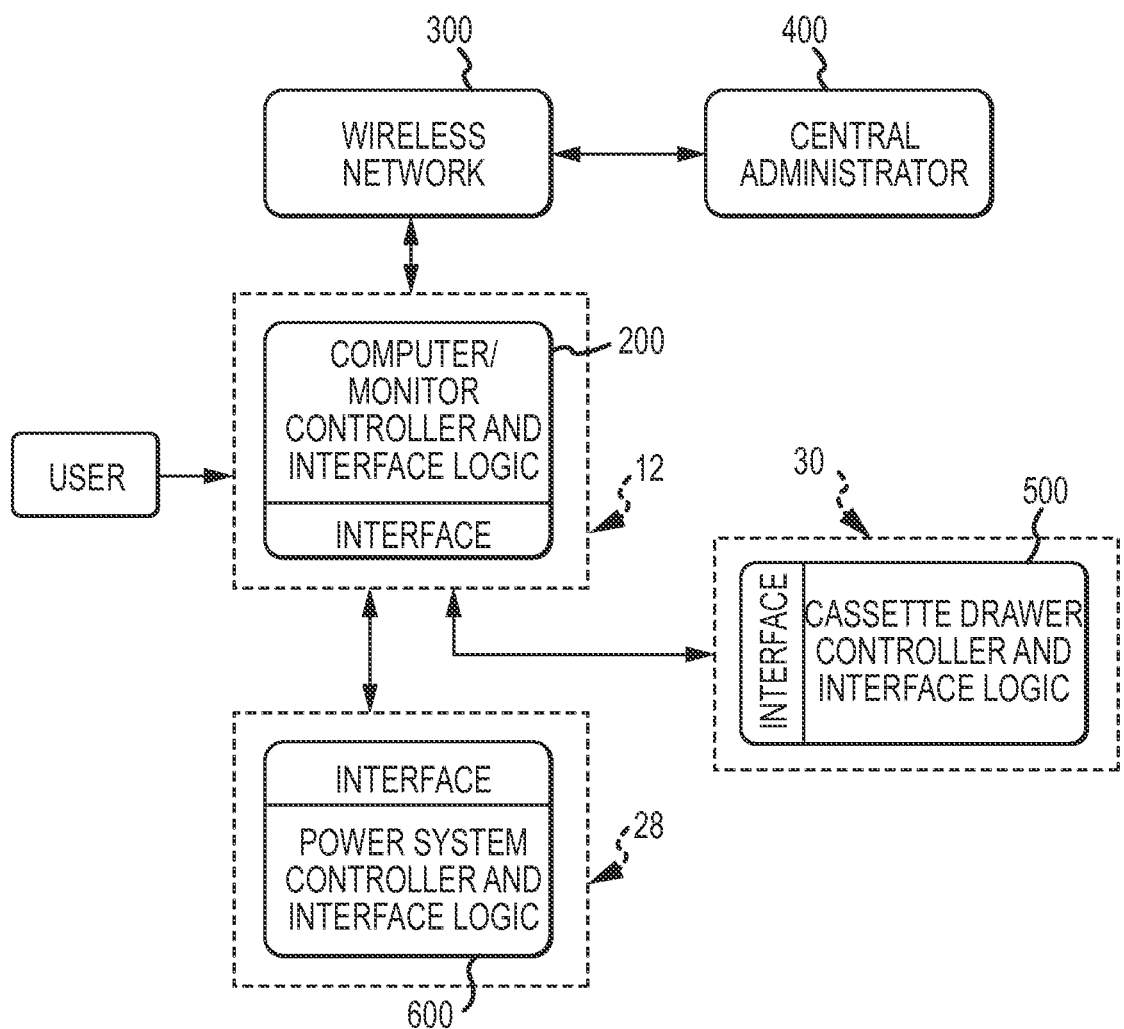
FIG. 6 illustrates a block diagram of an operating system that may be used for the medication dispensing cart of FIGS. 1A-C according to an embodiment of the invention.

Referring now to FIG. 6, illustrated is a block diagram of an operational system of cart 10 (e.g., cart 10's computer system). The operational system includes a computer controller and interface logic 200 that receives computer controller input and generates computer controller output. For example, computer controller 200 processes user input, such as the identity of user, the biometric information of user, pass codes entered by user, etc. and performs one or more cassette, bin, power, and/or batter related functions, such as: locking/unlocking bins, assigning cassettes and/or bins as patient-specific or utility specific, monitoring the status of cassettes and/or bins, identifying or determining the cassette stack configurations and/or cassette sizes, facilitating in loading and administration of medications, monitoring and/or adjusting battery power (e.g., current and/or voltage), monitoring battery status, monitoring and/or adjusting cart 10's power usage, decoupling unstable batteries, and/or any of the other functions described herein. Computer controller 200 may perform these various functions with the assistance of the various other controllers described herein and specifically shown and described in FIG. 6, such as the power system controller, the cassette controller, and the like. It should be realized that although the computer controller 200, cassette controller 500, and power system controller 600 are shown and generally described herein as separate control systems, in some embodiments cart 10's computer system comprises all these controllers or a single controller that performs the controller functions described herein.

The user information and/or access information (e.g., date, time, user, etc.) may be reported to the central administrator 400 so that cassette/bin access and/or user access may be monitored by the central administrator. Further, central administrator 400 may tie all the medication carts 10 in the system together and may tie all users in the system together so that a nurse's identifier and/or password is capable of unlocking and operating any of the medication carts 10 tied to the central administrator 400, thereby eliminating the need for passwords specific to each cart. Further, when a user is terminated from employment, central administrator 400 may render the user's identifier and password inoperable, thereby eliminating the possibility that the user may use their password to gain access to a cart.

Computer controller 200 may provide output to cassette system 30 via backplane 27 and/or cassette controller 500 relating to the designation of cassettes 76 and/or bins 94 included in the cassette system 30 (e.g., outputs patient cassette and/or bin assignments, patient specific bin assignments, utility bin assignments, etc.). The designation of cassettes 76 and/or patient specific bins 94 may be tied with the central administrator 400, such as a hospitals Admission Discharge Transfer (ADT) system so that cassettes 76 and/or bins 94 are automatically assigned by the ADT system upon admittance into the hospital and assignment to a bed. Depending upon the needs of the patient, the ADT system may assign multiple cassettes or bins and/or determine the size of the cassettes 76 needed (e.g., roughly 6 inch or roughly 3 inch cassettes). Further, the cassette and/or bin assignments may be automatically transferred by the ADT system as the patients is transferred between rooms and/or floors within the hospital. In some embodiments, the cassette/bin assignments are stored in a memory medium of the cassette (or centrally on a network) so that the assignment information is automatically uploaded to the cart 10's computer system (e.g., computer controller 200) when the cassette is plugged into a port 81 of backplane 27.

In another embodiment, the ADT system provides information about patients that have been assigned to the ward in which the nurse is working and one or more patients may be assigned to the nurse, such as by the nurse assigning the patients to themselves. When the nurse logs into the computer controller 200 (e.g., the cart's 10 control system), the system may provide the nurse with a listing of the patients in the ward. The nurse may select a patient and then select a cassette 76 and/or bin 94 from a display provided on touch screen 12 or may select an auto-assignment function in which the cart automatically assigns one or more cassettes 76 and/or bins 94. The patient's information (e.g., medical history, medication, room number, etc.) may be automatically provided to the cart 10 and associated with the assigned cassettes 76 and/or bins 94 so as to eliminate the need for the nurse to manually input any information. Cassette 76 and/or bin 94 selections/assignments may be provided to the central administrator 400, so that the cassette/bin assignment is monitored and/or recorded.

Information that is communicated to the cart and/or from the cart may be queued so that information that is not immediately deliverable may be subsequently delivered. For example, if the patient information, such as patient assignments, medical history, medications, and the like is provided to a specific medication cart 10 (i.e., computer/monitor controller) from central administrator 400, but is unable to be delivered due to power failure of the cart and/or network, the information may be queued so that upon returning online (either the cart or network or both), the information is resent to the medication cart 10. Likewise, each medication cart 10 may be fully operational despite the central administrator 400 and/or network (i.e., wireless network 300) going down. The cart 10 may have a redundant system in place so that when the cart becomes disconnected from the network, the cart is still fully operational, thereby allowing cart 10 to interact and record events, such as the battery status, cassette and/or bin status, access status, patient cassette and/or bin association, etc. When the central administrator 400 and/or network (e.g., wireless network 300) returns online or otherwise becomes available, medication cart 10 may communicate the information recorded while the central administrator and/or network was down. In this manner, the transition between cart functionality when the network and/or central administrator 400 is online and offline may be seamless or near seamless.

In addition, the operating system (e.g., cart 10's computer system) can, in real time, inventory medication as it is loaded into each bin 94 and as it used, as well as which user is dispensing the medication. Additionally, cart 10 may be equipped with a wireless network connection 300, preferably through SMTP (simple mail transfer protocol) so that the cart 10, or a user of that cart, can communicate with a central administrator 400 about conditions of the cart, such as a low battery, user access, and the like. Cart 10 may also communicate with administrator 400 without the active assistance of the user. Accordingly, the status and whereabouts of cart 10 can be constantly and effectively monitored through wireless communication along with the status of the batteries, user access history, and the like as described above.

As previously described, the cassette system 30 may also include cassette controller and interface logic 500, which may be housed in or otherwise communicatively coupled with backplane 27. This cassette controller 500 receives input from the computer controller 200 about the cassettes 76 and/or bins 94 and their designations and also automatically determines the size of the attached cassettes 76 and the configuration of the cassette system 30, which information may be relayed to computer controller 200. As described above, cassette controller 500 can lock and unlock bins 94 based upon receiving an authorized input and/or receiving an override input. Furthermore, the cassette controller 500 may log bin access and status, including when they are opened and by whom. Accordingly, the cassette system 30 has the ability to monitor itself. Similarly, power system 28 also includes power system controller and interface logic 600, which monitors the condition and/or charging of battery (s) 402. The power system controller 600 may also control the raising and lowering of post 24. The power system controller 600 may communicate with central administrator 400 to provide status information about the battery and/or other conditions of cart 10. Cart 10's computer system (e.g., touch screen 12) may also automatically report (e.g., via email, SMS, MMS, and the like) an attempt to break into cart 10, a log of the charging system, a log of the times and the identities of users who have accessed each cassette. Other information can also be reported.

Figure 7:
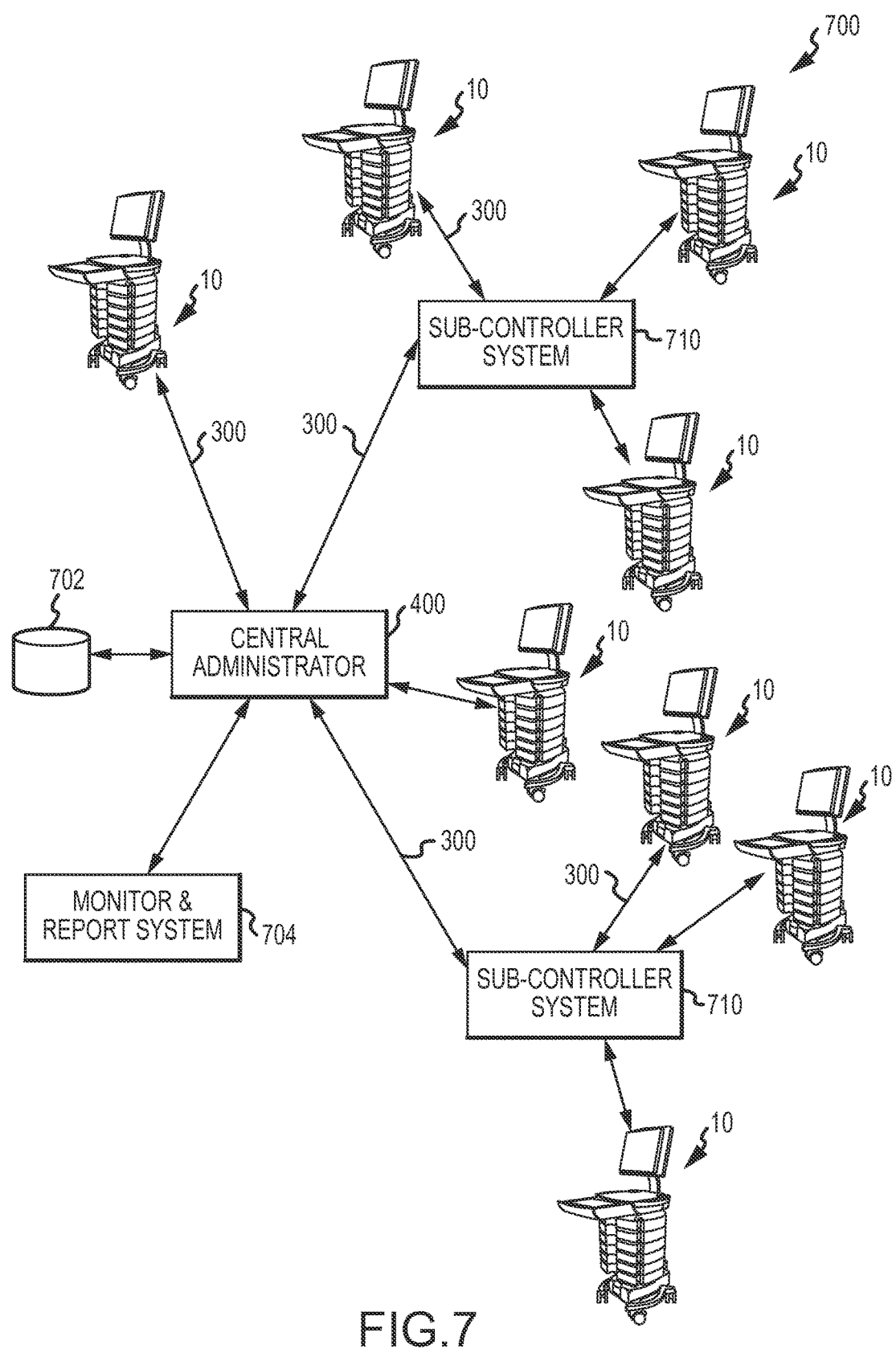
FIG. 7 illustrates a block diagram of a medication cart system according to an embodiment of the invention.

Illustrated in FIG. 7 is a simplified system 700 of a central administrator 400 that may centrally manage a plurality of medication carts 10. Central administrator 400 may be tied to a hospitals Admission Discharge Transfer (ADT) system, Pharmacy Information System (PIS), administration system, and/or Automated Dispensing Machine (ADM). Further, the central administrator may be a sub-component of the ADT/ADM system or may be a separate control system. Each of the medication carts 10 may include a power system controller, cassette controller, and computer/monitor controller as described above, which monitors information about various aspects of the cart (e.g., user access, cassette/bin access, battery status, patient information, unauthorized access, etc.). This information may be provided to the central administrator 400 so that the central administrator can centrally manage the real time status and historical status of each cart 10. In essence, the central administrator 400 is capable of monitoring and recording every event that occurs at the medication cart 10, such as the user access history (i.e., based on user identifier and/or password), battery history, cart location history (i.e., floor assignment), patient history, etc. Further, the central administrator may differentiate between events, such as differentiate between whether a bin 94 access occurs due to a nurse authentication (i.e., input user identifier and password) or a patient authentication (i.e., patient wristband scan and secondary identifier).

Further, the central administrator 400 may centrally manage the batteries used in the medication carts 10 and monitor the users that operate the carts. The information may be provided via one or more networks, such as wireless network 300 or a wired network. Further, the central administrator 400 may directly interact with the medication carts 10 (shown by the solid lines directly connecting central administrator 400 and carts 10) and/or may indirectly interact with the carts by interacting with a sub-controller system 710, which in turn directly interacts with the carts 10. For example, the medication carts 10 may directly interact with a sub-controller system 710 that is located on the floor or ward where the cart resides. The sub-controller system 710 may be controlled by the central administrator 400, such as the hospital administration system. Information exchanged between the cart 10 and the central administrator 400 may be routed through the sub-controller system 710 so that additional information (e.g., floor specific information) may be added and/or unnecessary information removed. Further, the central administrator 400 may quickly transfer or exchange information between carts 10, such as transferring patient information when a patient is transferred between floors.

The information provided to the central administrator 400 may be stored in a database 702, which may be remote from central administrator 400 or included therewith. The information may be stored for a predetermined amount of time (e.g., store information for a year). Further, central administrator 400 may be coupled with or include a monitoring and reporting system 704 that monitors real time and historical data about each cart 10 including: battery status and/or history (charge rate, discharge state, shutdown events), user access (logon, logoff), access events, bin access/activity (unlock, lock, open, close), etc. The monitoring and reporting system 704 may generate one or more email notifications/or paper reports (e.g., work orders) based on real time or historical events that occur (or have occurred), such as when a dead battery is detected, low battery is detected, an unauthorized cassette/bin access occurs, a patient medication schedule is missed, excessive and repeated bin access is observed, etc. The monitoring and reporting system 704 may further generate one or more reports based on system/cart audits performed. The auditing and/or monitoring parameters for batteries, users, access events, etc. may be predefined in the system so that reports are automatically generated when the parameters are exceeded.

Because central administrator 400 may be tied to the hospital's ADT, PIS, and/or ADM systems, information input into one of those systems may be immediately available and provided to the medication chart. For example, as medications are provided or updated by a pharmacist, the additions or modifications can immediately or nearly immediately be displayed, via the PIS, on touch screen 12 of medication cart 10. Likewise, dosage amounts and/or frequency input into touch screen 12 of cart 10 may be immediately available to the supervising physician or doctor. Medication cart 10 may be operable with pre-existing hospital systems so that no additional hardware and/or software is needed to integrate medication cart 10 into the system. Thus, carts 10 may be essentially plugged into and used with currently operating administration systems.

Figure 8:
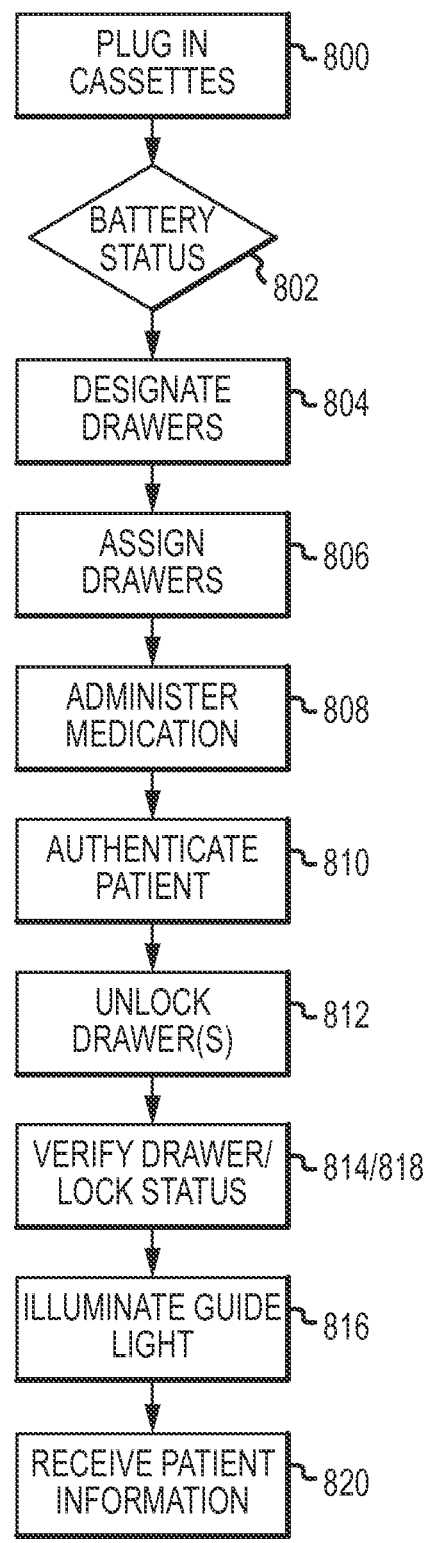
FIG. 8 illustrates a process for using a medication cart according to an embodiment of the invention.

Illustrated in FIG. 8 is a process flow diagram for operational use and features of the medication cart system. As shown, at block 800 one or more cassettes 76 or a cassette system 30 may be plugged into backplane 27. The cassette controller system and/or backplane 27 may automatically determine the type of each cassette 76 (i.e., large or small) and the configuration of the cassettes in the cassette system 30. At 802, a decision may be made by medication cart 10 about the status of the battery(s) 402 (e.g., charge level, operating condition, etc.). The battery 402 may perform a self-diagnostic test and provide the results to the power system controller via SMB connector 434 and SMB port 308. The power system controller may provide the battery status to the central administrator 400 via wireless network 300 so that the real time status and/or historical status of the battery may be monitored. If either battery 402 needs replacing, the battery(s) may be hot swapped for a newly charged battery or an external power source may be plugged into power system 28 to recharge the battery(s).

At 804, each of the bins 94 may be designated as patient specific or utility bins by the central administrator 400 and/or a nurse or other user of the medication cart 10. At block 806, one or more patients may be assigned to a cassette 76 and/or bin 94 by the central administrator 400 and/or nurse (e.g., the central administrator may assign the patient to a floor or a nurse and the medication cart 10 can auto assign the cassettes 76 and/or bins 94 of the cassette system 30). Upon assigning each cassette and/or bin, the patient's information may be automatically provided to the medication cart 10 from the central administrator and associated with the assigned cassettes/bins. The information about the bin 94 designations and/or bin assignments may be provided to the central administrator 400 via wireless network 300 (or a wired network), so that the central administrator can centrally manage all the cassette systems 30 and individual bins 94 along with managing hospital staff and patients.

Any reassignments of the bins or transfers of the patient can be provided to the central administrator 400 so that the central administrator is informed of the real time status of each bin 94 and/or cassette 76 and the patient is always assigned a bin. At block 808, as the nurse is administering medication or otherwise helping the patient, the bin associated with that patient may be unlocked. For example, the medication cart 10 may authenticate the nurse, such as by verifying a nurse identifier and password that is specific to the nurse. Upon authenticating the nurse, the nurse may select a patient from a touch screen display and the corresponding bin may be unlocked. Alternatively or additionally, at block 810, the nurse may scan the wristband or other identifier of the patient and/or provide a secondary identifier of the patient to unlock the patient's bin 94. The secondary identifier may include providing a confirmation that the patient displayed on monitor 12 is in fact the patient being treated, such as by selecting a confirmation button on the touch screen. At block 812, the bin controller and/or backplane 27 may control a locking mechanism (e.g., solenoid) to unlock the patient's bin).

In some embodiments, the patient's bin 84 may be unlocked in a bin management program displayed on touch screen 12 (e.g., when assigning drawers to patients) or when the patient is selected, such as by selecting the patient from a patient list (e.g., from ADT) or scanning a patient identifier on the patient's wrist band, and the like. In some embodiments, the patient's bin may be locked when the caregiver or user switches from a patient specific screen, selects another patient, logs off, and/or after a period of inactivity. In some embodiments, utility bins may be un-locked when a caregiver or user is authenticated into the system. These bins may remain un-locked while the caregiver or user is logged in and may lock when the caregiver or user logs out or after a period of inactivity.

At block 814, the bin controller and/or backplane 27 may verify, via one or more sensors, that the locking mechanism is disengaged and that the patient's bin 94 is in fact unlocked. At block 816, via bin controller or backplane 27, a guide light 90 may be illuminated on the patient's bin 94 to visually notify the nurse of the location of the patient's bin. Any utility bins may also be unlocked upon authenticating the nurse and/or patient. At block 818, the bin controller and/or backplane 27 may verify, via one or more sensors, the status of the bin 94 to determine whether a patient's bin is in fact open or closed. Information about the authentication of the nurse and/or patient and accessing of the bin may be provided, via wireless (or wired) network 300, to central administrator 400 so that the real time status of the patient, nurse, and/or bins 94 may be determined and the historical status may be monitored. Likewise, any malfunction of the medications cart 10, such as non-unlocking bins, non-opening or closing bins, power failure, etc. may be reported to the central administrator as well. Other information may also be reported, such as unauthorized access, etc.

At block 820, information about the patient may be input into the medication cart, via touch screen, keyboard, mouse, etc. This information may be provided to the central administrator 400. At block 822, one or more emails, reports, or other notifications may be generated and provided to an appropriate person or system in response to monitoring the cart, users, patients, etc. For example, an email may be provided to a hospital staff to change the cart's low battery or recharge the battery or a report may be generated to transfer a patient to a new floor based on a doctor's recommendation.

Figure 9:
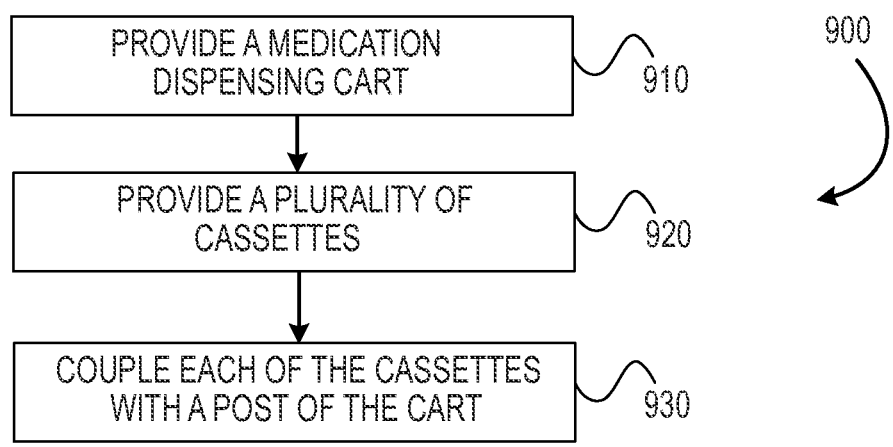
FIG. 9 illustrates a process for configuring a medication cart according to an embodiment of the invention.

Referring now to FIG. 9, illustrated is a method for configuring a medication dispensing cart. At block 910, a medication dispensing cart may be provided. The medication dispensing cart may include a cassette system controller, a base, a monitor that displays information to a user, and a post that couples the monitor with the base, such as those described herein. The post may have at least one interface port that communicatively couples the cassette system controller with one or more cassettes. At block 920, a plurality of cassettes may be provided that each include at least one bin within which medical supplies are stored. At block 930, each of the plurality of cassettes may be coupled with the post so that the plurality of cassettes form a cassette stack and so that at least one of the cassettes is communicatively coupled with the cassette system controller via the at least one interface port.

Figure 10:
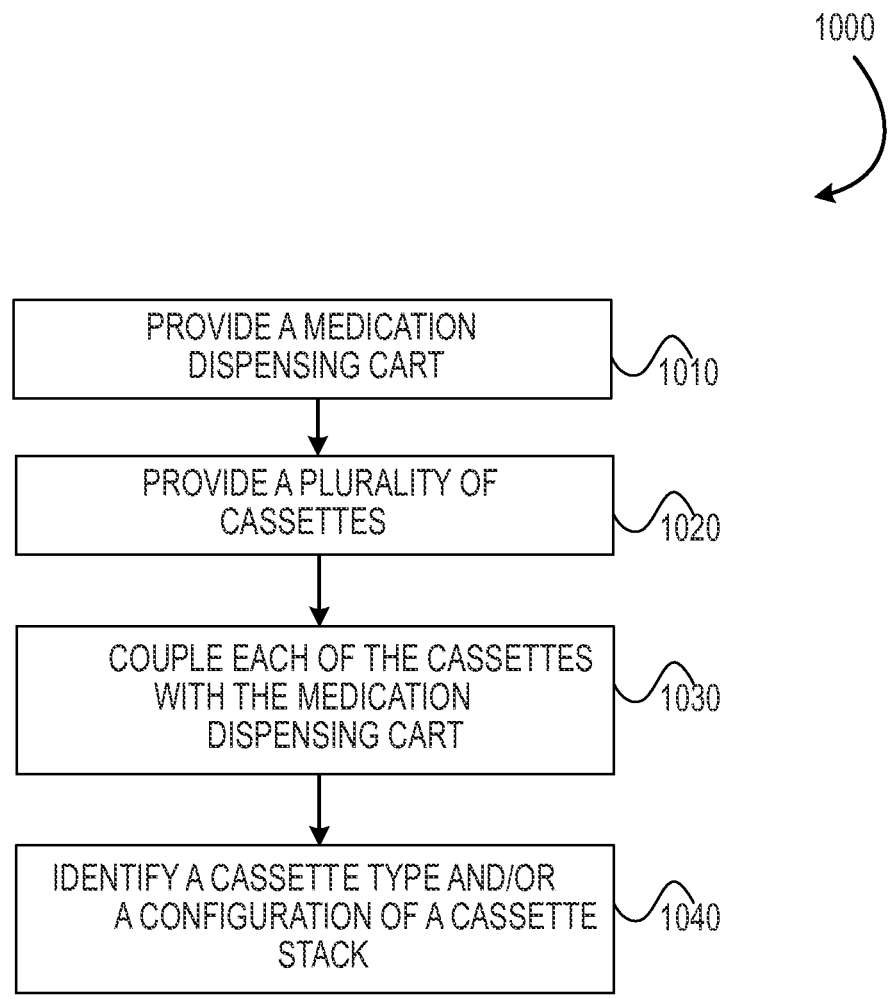
FIG. 10 illustrates another process for configuring a medication cart according to an embodiment of the invention.

Referring now to FIG. 10, illustrated is another method for configuring a medication dispensing cart. At block 1010, a medication dispensing cart is provided. The medication dispensing cart may include a cassette system controller. At block 1020, a plurality of cassettes are provided that each include at least one bin within which medical supplies are stored. At block 1030, each of the plurality of cassettes are coupled with the medication dispensing cart so that the plurality of cassettes form a cassette stack and so that at least one of the cassettes is communicatively coupled with the cassette system controller. At block 1040, the cassette system controller identifies a type of the at least one cassette communicatively coupled with the cassette system controller and/or a configuration of the cassette stack.

Figure 11:
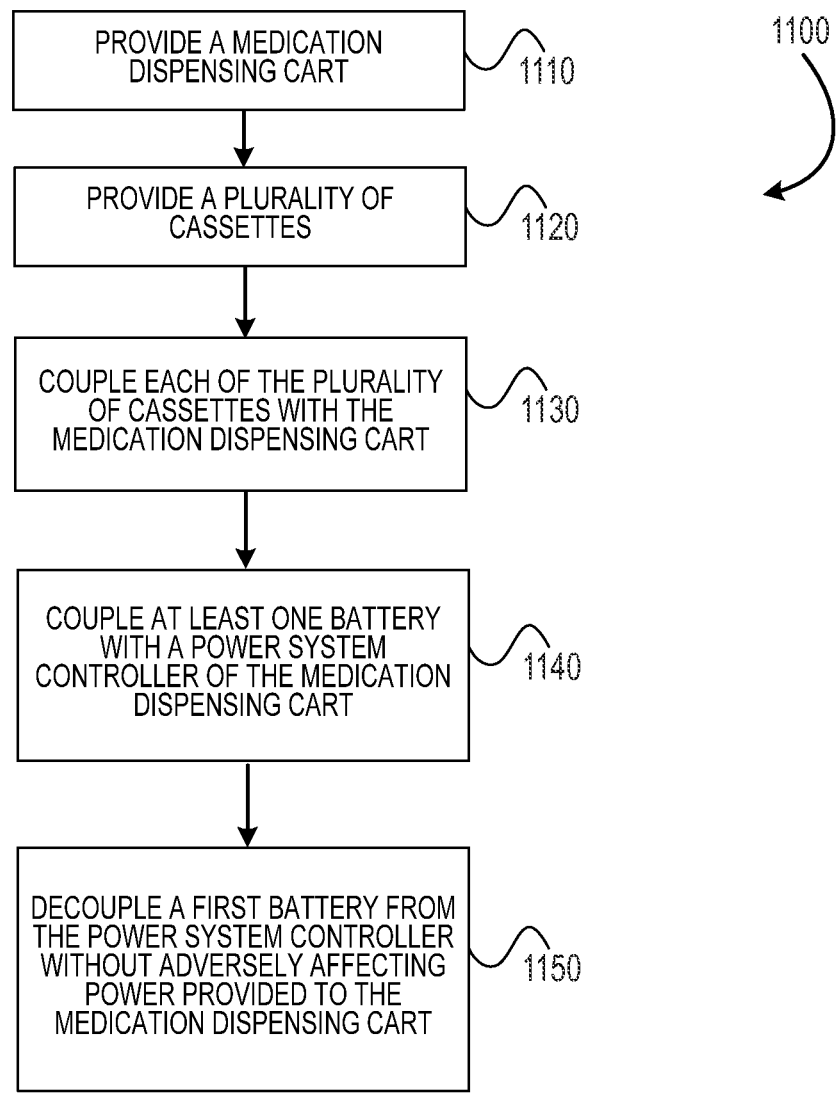
FIG. 11 illustrates a method for powering a medication dispensing cart according to an embodiment of the invention.

Referring now to FIG. 11, illustrated is a method of providing power to a medication dispensing cart. At block 110, a medication dispensing cart is provided. The medication dispensing cart may include a power system controller. At block 1120, a plurality of cassettes are provided that each include at least one bin within which medical supplies are stored. At block 1130, each of the plurality of cassettes are coupled with the medication dispensing cart. At block 1140, at least one battery is coupled with the power system controller. The power system controller may be configured to adjust a power usage of the medication dispensing cart or adjust a power discharge of the at least one battery based on an operational need of the medication dispensing cart or a condition of the battery.

In some embodiments, the medication dispensing cart may include at least two batteries coupled with the power system controller and the method may also include decoupling a first battery from the power system controller while the medication dispensing cart is operational, or being operated, without adversely affecting an amount of power provided to the medication dispensing cart. The first battery may be a hot swappable battery and/or smart battery as described herein so that the battery may be removed from the medication dispensing cart and inspected, recharged, replaced, repaired, and the like. The battery may also communicate with the power system controller regarding a charge and/or discharge status, a problem, and the like. One or more settings or conditions of the battery may be adjusted by the power system controller and/or the battery itself based on the information communicated to the power system controller. The battery may be removed from the medication dispensing cart while the cart is being operated based entirely or substantially off battery power.

In some embodiments, the medication dispensing cart may also include a cassette system controller and the plurality of cassettes may be coupled with the medication dispensing cart so that at least one of the cassettes is communicatively coupled with the cassette system controller. In such embodiments, the method may further include identifying (with the cassette system controller) a type of the at least one cassette communicatively coupled with the cassette system controller and/or a configuration of the cassette stack.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A medication dispensing cart comprising:
    a base having wheels that allow the medication dispensing cart to be moved within a facility;
    a computing device configured to receive input from a user;
    a display device communicatively coupled with the computing device for displaying information to the user;
    a post that attaches the display device with the base so that the post, display device, and base are moveable within the facility as a single/stand-alone unit, the post comprising an outer post member that slidingly receives an inner post member in a manner that enables vertical adjustment of the post, the outer post member including an electrical backplane having a plurality of communication ports positioned along a longitudinal length thereof, wherein each communication port is communicatively coupled with the computing device; and
    a plurality of cassettes or drawers that each have at least one bin within which medical supplies are stored, wherein each cassette or drawer is removably coupled with the outer post member, and wherein each cassette or drawer includes a connector that is insertable within a respective communication port of the outer post member to communicatively couple the respective cassette or drawer with the computing device so that electrical signals may be transmitted between the cassette and the computing device.

2. The medication dispensing cart of claim 1, wherein one or more of the plurality of cassettes comprise a guide light configured to illuminate to display a location of a bin of the cassette.

3. The medication dispensing cart of claim 1, further comprising a stand-by button that sets the display device in a stand-by mode when activated, wherein information is not displayed on the display device in the stand-by-mode.

4. The medication dispensing cart of claim 3, further comprising a stand-by indicator configured to display a first display when the display device is in the stand-by mode and a second display when the display device is not in the stand-by mode.

5. The medication dispensing cart of claim 1, further comprising a power system controller and at least one battery, wherein the power system controller is configured to adjust the power usage of the medication dispensing cart or adjust a power discharge setting of the battery based on an operational need of the medication dispensing cart or a condition of the battery.

6. The medication dispensing cart of claim 5, further comprising two batteries that provide power to the medication dispensing cart, wherein one of the batteries is removable from the medication dispensing cart without adversely affecting the power provided to the medication dispensing cart.

7. The medication dispensing cart of claim 5, further comprising a housing within which the battery is inserted, wherein the housing comprises a latch mechanism to lock the battery within the housing.

8. The medication dispensing cart of claim 5, wherein the at least one battery comprises a hot swappable smart battery, and wherein the power system controller comprises an interface port that communicatively couples the power system controller with the smart battery.

9. The medication dispensing cart of claim 8, wherein the smart battery comprises a gauge to generate readings of the battery's remaining capacity.

10. The medication dispensing cart of claim 5, further comprising a backup battery configured to allow access to one or more bins during a power failure of the medication dispensing cart or to determine when unauthorized access to one or more bins occurs after a power failure of the medication dispensing cart.

11. The medication dispensing cart of claim 1, wherein the cassettes are coupled with the outer post member to form a cassette stack, and wherein the cassette stack comprises a combination of large cassettes and small cassettes.

12. The medication dispensing cart of claim 11, wherein the large cassettes comprise bins ranging in height between about 4 inches and about 8 inches, and wherein the small cassettes comprise bins ranging in height between about 2 inches and about 4 inches.

13. The medication dispensing cart of claim 1, wherein the computing device is configured to determine a cassette configuration of the plurality of cassettes via coupling of the respective connectors with the respective communication ports of the outer post member.

14. The medication dispensing cart of claim 1, wherein the display device comprises a discharge element coupled to a touch screen, the discharge element being configured to dissipate a static charge generated by a user of the medication dispensing cart or the touch screen.

15. The medication dispensing cart of claim 1, wherein the medication dispensing cart is one of a plurality of medication dispensing carts wirelessly networked with a central administrator system.

16. The medication dispensing cart of claim 1, wherein at least one of the plurality of cassettes is non-removably coupled with the medication dispensing cart.

17. A method of providing a medication dispensing cart comprising:
    providing a medication dispensing cart comprising:
        a cassette system controller;

a base having wheels that allow the medication dispensing cart to be moved within a facility;

a display device that displays information to a user; and a post that attaches the display device with the base so that the post, display device, and base are moveable within the facility as a single unit, the post including an electrical backplane having a plurality of communication ports positioned along a longitudinal length thereof, wherein each communication port is communicatively coupled with the cassette system controller;

providing a plurality of cassettes that each include a top surface, a bottom surface, two sides extending between the top and bottom surfaces, and a back that includes a recess defining a vertical channel that extends through at least a portion of the top and bottom surfaces, wherein each cassette further includes at least one bin configured to store medical supplies and a plug or connector;

coupling each cassette with the post by positioning the post within the recess of the respective cassette so that the post extends vertically through the vertical channel and so that at least a portion of the post is recessed relative to the back of the respective cassette; and communicatively coupling each cassette with the cassette system controller by inserting the plug or connector of the cassette into a respective communication port of the backplane so that electrical signals may be transmitted between the cassette and the cassette system controller, wherein the post, display device, and base are moveable within the facility as the single unit while the plug or connector of each cassette or drawer is inserted within the respective communication port of the backplane.

18. The method of claim 17, wherein the plurality of cassettes are coupled with the post so that the plurality of cassettes form a cassette stack.

19. The method of claim 17, further comprising identifying with the cassette system controller a type of the at least one cassette communicatively coupled with the cassette system controller.

20. The method of claim 17, further comprising identifying with the cassette system controller a configuration of a cassette stack upon coupling of the respective connectors with the respective communication ports.

21. The method of claim 19, further comprising configuring the cassette system controller to operate with the at least one cassette based off the identification of the type of the at least one cassette.

22. The method of claim 19, wherein identifying the type of the at least one cassette comprises identifying one or more of the following selected from the group consisting of:
determining a size of the cassette from among a plurality of different sized cassettes;
determining that the cassette comprises a patient-specific bin; and
determining that the cassette comprises a utility specific bin.

23. The method of claim 20, wherein identifying a configuration of the cassette stack comprises determining an arrangement of different sized cassettes in the cassette stack or comprises determining an association between a patient and a cassette designated to store medical supplies specifically for the patient.

24. A medication dispensing cart comprising:
a base having wheels that allow the medication dispensing cart to be moved within a facility;
a computing device configured to receive input from a user;
a display device communicatively coupled with the computing device for displaying information to the user;
a plurality of cassettes or drawers that each have at least one bin within which medical supplies are stored, wherein at least one of the plurality of cassettes or drawers is communicatively coupled with the computing device via a communication port; and
a battery housing coupled with the base, the battery housing including a pair of slots within which a battery is inserted, wherein each slot faces upward from the base to allow a respective battery to be inserted within a respective slot from above the base.

25. The medication dispensing cart of claim 24, wherein each slot of the battery housing further comprises a latch mechanism to lock the respective battery within the respective slot.

26. The medication dispensing cart of claim 24, wherein the battery housing is coupled with a rear surface of the base.

27. The medication dispensing cart of claim 24, wherein each battery inserted within the pair of slots is capable of powering the medication dispensing cart such that one of the batteries is removable from the battery housing without adversely affecting the power provided to the medication dispensing cart.

28. The medication dispensing cart of claim 24, further comprising a post that attaches the display device with the base, the post comprising a plurality of communication ports that are positioned along a longitudinal length of the post, wherein each communication port is communicatively coupled with the computing device, and wherein each cassette or drawer includes a plug or connector that is inserted within a respective communication port of the post to communicatively couple the respective cassette or drawer with the computing device.

29. The medication dispensing cart of claim 28, wherein the plurality of communication ports are coupled with a backplane of the post.

30. The medication dispensing cart of claim 24, wherein the cassettes are coupled with the post to form a cassette stack, and wherein the cassette stack comprises a combination of large cassettes and small cassettes.

* * * * *